US008197819B2

(12) United States Patent
Srivastava et al.

(10) Patent No.: US 8,197,819 B2
(45) Date of Patent: Jun. 12, 2012

(54) ENV POLYPEPTIDE COMPLEXES AND METHODS OF USE

(75) Inventors: Indresh K. Srivastava, Benicia, CA (US); Victoria Sharma, Orinda, CA (US); Susan W. Barnett, San Francisco, CA (US); Jeffrey Ulmer, Danville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 1031 days.

(21) Appl. No.: 11/597,337

(22) PCT Filed: Jun. 8, 2005

(86) PCT No.: PCT/US2005/022808
§ 371 (c)(1),
(2), (4) Date: Dec. 28, 2007

(87) PCT Pub. No.: WO2005/121175
PCT Pub. Date: Dec. 22, 2005

(65) Prior Publication Data
US 2008/0199492 A1    Aug. 21, 2008

Related U.S. Application Data

(60) Provisional application No. 60/578,445, filed on Jun. 8, 2004, provisional application No. 60/578,211, filed on Jun. 8, 2004.

(51) Int. Cl.
*A61K 39/21* (2006.01)
*A61K 39/00* (2006.01)
*C07D 207/00* (2006.01)
*C07D 487/00* (2006.01)

(52) U.S. Cl. ............... 424/188.1; 424/184.1; 424/187.1; 424/208.1; 548/541; 532/11

(58) Field of Classification Search .................. None
See application file for complete search history.

(56) References Cited

OTHER PUBLICATIONS

Biorn AC, et al. "Mode of action for linear peptide inhibitors of HIV-1 gp120 interactions." Biochemistry. Feb. 24, 2004;43(7):1928-38.*
Si "Small-molecule inhibitors of HIV-1 entry block receptor-induced conformational changes in the viral envelope glycoproteins" PNAS 101(14)5036-5041; 2004.*
Wang et al. "Discovery of 4-Benzoyl-1-[(4-methoxy-1Hpyrrolo[2,3-b]pyridin-3-yl)oxoacetyl]-2- (R)-methylpiperazine (BMS-378806): A Novel HIV-1 Attachment Inhibitor That Interferes with CD4-gp120 Interactionst" (J. Med. Chem. 46:4236-4239, 2003).*
Schön A. et al. "Binding Thermodynamics of a Small-Molecular-Weight CD4 Mimetic to HIV-1 gp120" Biochemistry. Sep. 12, 2006; 45(36): 10973-10980.*
Barr et al., "Antigenicity and immunogenicity of domains of the human immunodeficiency virus (HIV) envelope polypeptide expressed in the yeast *Saccharomyces cerevisiae*," Vaccine, vol. 5, Jun. 1987, pp. 90-101.
Biorn et al., Mode of Action for Linear Peptide Inhibitors of HIV-1 gp120 Interactions, American Chemical Society, vol. 43, 2004, pp. 1928-1938.
Dowd et al., "Beta-Turn Phe in HIV-1 Env Binding Site of CD4 and CD4 Mimetic Miniprotein Enhances Env Binding Affinity but Is Not Required for Activation of Co-Receptor/17b Site," Biochemistry 2002, vol. 41, No. 22, p. 7038-7046.
Dowd et al., "CD4 mimetic peptides and the mechanism of HIV entry, "Abstracts of Papers, American Chemical Society, vol. 221, No. 1-2, 2001, p. MEDI 114.
Finnegan et al., "Antigenic Properties of the Human immunodeficiency Virus Envelope during Cell-Cell Fusion," The Journal of Virology, 2001, vol. 75, No. 22, p. 11096-11105.
Fouts et al. "Crosslinked HIV-I envelope-CD4 receptor complexes elicit broadly cross-reactive neutralizing antibodies in rhesus macaques," Proceedings of National Academy of Sciences of United States of America, Epub, Aug. 21, 2002, vol. 99, No. 18, p. 11842-11847.
Guo et al., "Biochemical and genetic characterizations of a novel human immunodeficiency virus type 1 inhibitor that blocks gp120-CD4 interactions," Journal of Virology, vol. 77, No. 19. Oct. 2003, pp. 10528-10536.
International Search Report for PCT/US2005/022808 mailed May 5, 2008.
Li et al., "Phage randomization in a charybdotoxin scaffold leads to CD4-mimetic recognition motifs that bind HIV-1envelope through nonaromatic sequences," The Journal of Peptide Research, 2001, vol. 57, p. 507-518.
Lin et al., "A small molecule HIV-1 inhibitor that targets the HIV-1 envelope and inhibits CD4 receptor binding," PNAS, vol. 100, No. 19, Sep. 16, 2003, pp. 11013-11018.
Martin et al., "Rational design of a CD4 mimic that inhibits HIV-1 entry and exposes cryptic neutralization epitopes," Nature Biotechnology, vol. 21, No. 1, Jan. 1, 2003, pp. 71-76.
Reeves et al., "Emerging drug targets for antiretroviral therapy," Drugs, vol. 65, No. 13, 2005, pp. 1747-1766.
Schön et al., "Binding Thermodynamics of a Small-Molecular-Weight CD4 Mimetic to HIV-1 gp120," Biochemistry, vol. 45, No. 36, Sep. 12, 2006, pp. 10973-10980.
Si et al., "Small-molecule inhibitors of HIV-1 entry block receptor-induced conformational changes in the viral envelope glycoproteins," PNAS, vol. 101, No. 14, Apr. 6, 2004, pp. 5036-5041.
Srivastava et al., "Role of neutralizing antibodies in protective immunity against HIV," Human Vaccines 2005 Mar.-Apr., vol. 1, No. 2, Mar. 2005, pp. 45-60.

(Continued)

*Primary Examiner* — Bo Peng
(74) *Attorney, Agent, or Firm* — Regina Bautista; Helen Lee

(57) ABSTRACT

Provided herein are small molecule CD4 mimetics effective to bind to HIV Env proteins. A CD4 mimetic of the invention, when bound to an Env protein, is effective to induce a conformational change in the Env protein such that cyptic epitopes on the Env protein are exposed. Also provided herein are related methods of identifying and using such small molecule CD4 mimetics, for example, to elicit an immune response in a subject upon administration.

10 Claims, 6 Drawing Sheets

OTHER PUBLICATIONS

Supplementary European Search Report for Application No. EP 05 78 6186, completed Jul. 30, 2009.
Wang et al., "Discovery of 4-Benzoyl-1-[(4-methoxy-1*H*-pyrrolo[2,3=*b*]pyridine-3-yl)oxoacetyl]-2-(*R*)-methylpiperazine (BMS-378806): A Novel HIV-1 Attachment Inhibitor That Interferes with CD4-gp120 Interactions," J. Med. Chem, vol. 46, 2003, pp. 4236-4239.

Zhang et al., "Antibody 17b Binding at the Coreceptor Site Weakens the Kinetics of the Interaction of Envelope Glycoprotein gp 120 with CD4," Biochemistry, vol. 40, 2001, p. 16621670.
Zhao et al., "Identification of N-phenyl-$N_1$-(2,2,6,6-tetramethyl-piperidin-4-yl)-ox alamides as a new class of HIV-1 entry inhibitors that prevent gp120 binding to CD4," Virology, vol. 339, No. 2, Sep. 1, 2005, pp. 213-225.

* cited by examiner

| Sample Name | BIACORE 1 % INHIBITION | BIACORE 2 % INHIBITION | BIACORE 3 % INHIBITION | HPLC1 % INHIBITION | HPLC2 % INHIBITION | HPLC3 % INHIBITION | BIACORE1 % UPREGULATION | BIACORE2 % UPREGULATION | BIACORE3 17B % UPREGULATION | BIACORE3 48D % UPREGULATION |
|---|---|---|---|---|---|---|---|---|---|---|
| GP 120/10uM MC34A | 21.8% | 27.1% | 53.6% | 10.0% | 7.9% | | -7.4% | -12.7% | -74.1% | -81.3% |
| GP 120/2.5uM CD4 | 68.1% | 95.6% | 93.7% | 87.3% | 87.5% | | 36.4% | 35.6% | 60.3% | 54.1% |
| GP 120/5uM CD4M33 | 57.3% | 85.1% | 86.6% | 63.2% | 63.9% | | 21.1% | 28.6% | 37.3% | 49.3% |
| UPREGULATES 17B (AND 4.8D) | | | | | | | | | | |
| 2 | | | | | | | | X | X | X |
| 20 | | X | | | X | | | | | |
| 21 | | X | | | X | | | | | |
| 22 | | | | | X | | | | | |
| 23 | | | | | X | | | | | |
| UPREGULATES 17B | | | | | | | | | | |
| INHIBITS CD4/UPREGS 17B | | | | | | | | | | |
| 19 | X | X | | X | | ND | | X | X | X |
| 23 | X | X | | ND | |

CD4 binding 17b binding

CD4 binding 17b binding

CD4 binding 17b binding 4.8d binding

ENV POLYPEPTIDE COMPLEXES AND METHODS OF USE

RELATED APPLICATIONS

This application is the U.S. National Phase of International Application No. PCT/US2005/022808, filed Jun. 8, 2005 and published in English, which claims the benefit of U.S. Provisional Application No. 60/578,445, filed Jun. 8, 2004, and U.S. Provisional Application No. 60/578,211, filed Jun. 8, 2004. The above applications are incorporated herein in their entirety by reference.

STATEMENT OF GOVERNMENT SUPPORT

The application was made with support of support from the United States NIAID-NIH HIVRAD under Grant No. 5P01 AI48225-03. Thus, the U.S. Government may have certain rights in this invention.

TECHNICAL FIELD

The invention relates generally to CD4 mimetics including peptoids, small molecules, and peptoid-small molecule conjugates that bind to HIV Env proteins and induce a conformational change in such Env proteins. More particularly, the invention relates to small molecules that induce conformational changes in Env polypeptides (such as monomeric or oligomeric gp120, gp140 or gp160) such that conserved, cryptic epitopes participating in Env-CD4 and chemokine receptor binding are exposed. The invention also pertains to methods of using these molecules to elicit an immune response against a broad range of HIV subtypes.

BACKGROUND

The human immunodeficiency virus (HIV-1, also referred to as HTLV-III, LAV or HTLV-III/LAV) is the etiological agent of the acquired immune deficiency syndrome (AIDS) and related disorders. (see, e.g., Barre-Sinoussi, et al., (1983) *Science* 220:868-871; Gallo et al. (1984) *Science* 224:500-503; Levy et al., (1984) *Science* 225:840-842; Siegal et al., (1981) *N. Engl. J. Med.* 305:1439-1444; Guyader et al., (1987) *Nature* 326:662-669).

The envelope protein of HIV-1, HIV-2 and SIV is a glycoprotein of about 160 kd (gp160). During virus infection of the host cell, gp160 is cleaved by host cell proteases to form gp120 and the integral membrane protein, gp41. The gp41 portion is anchored in the membrane bilayer of virion, while the gp120 segment protrudes into the surrounding environment. gp120 and gp41 more covalently associated and free gp120 can be released from the surface of virions and infected cells. Furthermore, upon binding to its receptor, CD4, the Env polypeptide undergoes a significant structural rearrangement. After this conformational change the CCR5 co-receptor binding site is exposed. Exposure of the CCR5 binding site, in turn, mediates viral entry into the host cell. See, e.g., Wyatt, R., et al. (1998) *Nature* 393:705-711; Kwong, P., et al. (1998) *Nature* 393:648-659.

Env appears to be the primary target for inducing a humoral immune response to HIV. However, it is known that antibodies directed against gp120 do not generally exhibit broad antibody responses against different HIV strains and do not induce production of neutralizing antibodies. See, e.g., Javaherian, K., et al. (1989) *Proc. Natl. Acad. Sci.* 86:6786-6772; Matsushita, M., et al. (1988) *J. Virol.* 62:2107-2144; Putney, S., et al. (1986) *Science* 234:1392-1395; Rushe, J. R., et al. (1988) *Proc. Nat. Acad. Sci. USA* 85:3198-3202; Matthews, T. (1986) *Proc. Natl. Acad. Sci. USA.* 83:9709-9713; Nara, P. L., et al. (1988) *J. Virol.* 62:262-2628; Palker, T. J., et al. (1988) *Proc. Natl. Acad. Sci. USA.* 85:1932-1936).

Furthermore, although neutralizing antibodies are typically generated in the course of HIV infection in humans, these antibodies do not provide permanent antiviral effect. This may in part be due to the generation of "neutralization escapes" virus mutants and to the general decline in the host immune system associated with pathogenesis. See, e.g., Barre-Sinoussi, F., et al. (1983) *Science* 220:868-871; Robert-Guroff, M., et al. (1985) *Nature* (London) 316:72-74; Weis, R., et al. (1985) *Nature* (London) 316:69-72; Weis, R., et al. (1986) *Nature* (London) 324:572-575. Nonetheless, it is widely believed that the presence of pre-existing neutralizing antibodies upon initial HIV-1 exposure will likely have a protective effect, for instance by attaching to the incoming virions and reducing or preventing their infectivity for target cells and prevent the cell-to-cell spread of virus in tissue culture. See, e.g., Hu et al. (1992) *Science* 255:456-459; Burton, D., R. and Montefiori, D. (1997) *AIDS* 11(suppl. A): 587-598; Montefiori and Evans (1999) *AIDS Res. Hum. Ret.* 15(8):689-698; Bolognesi, D. P., et al. (1994) *Ann. Int. Med.* 8:603-611; Haynes, B., F., et al. (1996) *Science* 271:324-328.

Several categories of potentially effective neutralizing antibodies have been identified. For example, in most infected individuals, a subset of broadly reactive antibodies that interfere with binding of gp120 and CD4 have been identified. See, e.g., Kang, C.-Y., et al. (1991) *Proc. Natl. Acad. Sci. USA.* 88:6171-6175; McDougal, J. S., et al. (1986) *J. Immunol.* 137:2937-2944. Other antibodies are believed to bind to the chemokine receptor-binding region after CD4 has bound to Env. See, e.g., Thali et al. (1993) *J. Virol.* 67:3978-3988). Monoclonal antibodies, such as IgG1b12, 2G12 (Mo et al. (1997) *J. Virol.* 71:6869-6874), PA14, (Trkola et al. (2001) *J. Virol.* 75(2):579-88) and 2F5, which are directed to the CD4 binding site, also exhibit neutralizing effects. See, also, Trkola et al. (1995) *J. Virol.* 69:6609-6617; D'Sousa et al (1997) *J. Infect. Dis.* 75:1062-1075. Furthermore, in order to generate antibodies against the CD4 binding site region, which is exposed only upon binding to CD4, several groups have attempted to generate neutralizing antibodies by administering complexes of Env bound to CD4 (e.g., soluble CD4, referred to as "sCD4") or to CD4 mimetics. See, e.g., Martin et al. (2003) *Nat Biotechnol.* 21(1):71-6. However, administration of unadjuvanted sCD4 alone is not immunogenic and adjuvanted sCD4 administration may trigger potentially devastating autoimmune responses.

Therefore, there remains a need for additional molecules, which, when administered to a subject, are capable of triggering a conformational change in Env proteins such as gp120. This induced conformational change is effective to expose cryptic epitopes on the Env protein to thereby generate a neutralizing antibody response—without the negative effects of adjuvanted sCD4.

SUMMARY

The present invention solves these and other problems by providing CD4 mimetics that complex with Env to expose epitopes in or near the CD4 binding site, and induce production of neutralizing antibodies. Also provided are compositions and complexes of Env with the CD4 mimetics described herein, as well as antibodies directed against these complexes.

In one aspect, the invention provides an immunogenic composition comprising an Env polypeptide and a small molecule CD4 mimetic having a molecular weight of less than about 1000 daltons. The CD4 mimetic present in the composition interacts with the Env polypeptide to form an Env polypeptide/CD4 mimetic complex comprising an exposed cryptic epitope.

Also provided is an immunogenic composition comprising an Env polypeptide/CD4 mimetic complex arising from the Env polypeptide and small molecule CD4 mimetic described above.

In one embodiment of the invention, the binding affinity of a cryptic epitope antibody such as Mab 17b or 48D to an Env polypeptide/CD4 mimetic complex of the invention is greater than the binding affinity of such cryptic epitope antibody to the Env polypeptide alone.

In another embodiment, an Env polypeptide/CD4 mimetic complex of the invention exhibits at least 1% percent upregulation of the 17b epitope or the 48D epitope when compared to the Env polypeptide alone.

Env polypeptides of the invention include polypeptides such as gp120, gp140 and gp160.

In another embodiment, the small molecule CD4 mimetic possesses a molecular weight selected from the following: about 900 daltons or less, about 800 daltons or less, about 750 daltons or less, about 700 daltons or less, about 600 daltons or less, and about 500 daltons or less.

In a further embodiment, the small molecule is covalently attached, optionally via an intervening spacer, to a cross-linking moiety.

The invention further includes an immunogenic composition comprising a small molecule that is crosslinked to an Env polypeptide to form a covalently bound Env polypeptide/CD4 mimetic complex.

In another embodiment, the small molecule CD4 mimetic comprises a fused bicyclic or tricyclic core structure. Such core structures include an indole, a pyrrolopyridine, and a fluoren-9-one.

More particularly, in another embodiment, the small molecule comprises a core structure selected from:

V and

VI where in structure V, none or one of ring carbons 4, 5, 6, or 7 may be replaced by a nitrogen.

In an additional embodiment related to the above, in each of core structures V and VI, one of the ring atoms is covalently attached, via an optional linker, J, to a substituted or unsubstituted piperidine or piperazine, which itself may form part of a bicyclic ring system such as a 1,2,3,4-tetrahydro-isoquinoline.

Additional embodiments related to the small molecule CD4 mimetics of the invention include the following.

For example, in either of V and VI, one of the ring atoms may be covalently attached, via an optional linker, J, to 3-oxomethylene-2-(1,2,3,4-tetrahydro-isoquinolin-1-ylmethyl)-2,3-dihydro-isoindol-1-one.

In a further embodiment, the core structure V is selected from the group consisting of 1-H indole, 1H-pyrrolo[2,3,-b]pyridine, 1H-pyrrolo[2,3,-c]pyridine, 1H-pyrrolo[3,2,-b]pyridine, and 1H-pyrrolo[3,2-c]pyridine.

In another embodiment, in each of core structures V and VI, any one of the ring atoms at position 2, 3, 6, or 7 is covalently attached, via an optional linker, J, to a substituted or unsubstituted piperidine or piperazine, which itself may form part of a bicyclic ring system.

In a further embodiment, in addition to the substituted or unsubstituted piperidine or piperazine, core structures V and VI each possess one or more optional substituents at the remaining ring atom positions. Such one or more optional substituents include $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, halogen, —CN, phenyl benzyl, nitro, $C_1$-$C_6$ alkoxy, $C_3$-$C_6$ cycloalkoxy, benzyloxy, —C(O)—$C_1$-$C_6$ alkyl, —C(O)—$C_6H_5$—, and —C(O)—$C_6H_4$—W, wherein W is an ortho, meta, or para-halogen.

In another embodiment, the optional linker, J, is from about one to 30 atoms in length. Illustrative linkers include —C(O)CH$_2$— —C(O)—, —C(O)—CHCH$_3$—, —C(O)—C(O)—, —CH(OH)CH$_2$—, —CH$_2$—, —N—C(O)-furanyl, in either orientation.

In another embodiment, a small molecule CD4 mimetic in accordance with the invention includes compounds 1-30 herein.

In another embodiment, a composition of the invention further includes an adjuvant.

In another aspect, the invention includes a method of eliciting an immune response in a subject. In the method, any one or more of the herein described immunogenic compositions is administered to a mammalian subject to thereby elicit an immune response therein, wherein the Env protein and CD4 mimetic are administered simultaneously, sequentially in any order, separately, or as a complex.

In a particular embodiment, the method includes administering an Env polypeptide such as a gp120 polypeptide.

In another embodiment, the method includes administering an Env polypeptide and a small molecule CD4 mimetic such that the CD4 mimetic interacts with the Env polypeptide to expose the CD4i cryptic epitope on the resulting Env polypeptide/CD4 mimetic complex. In a related embodiment, the method is effective to elicit in a mammalian subject the cellular production of antibodies to CD4i.

In another aspect, also provided is a method of identifying a CD4 mimetic capable of interacting with an Env polypeptide to expose a cryptic epitope on the Env polypeptide. The method includes the steps of a) providing an Env polypeptide; b) providing a candidate small molecule having a molecular weight of less than about 1000 daltons; c) contacting the Env polypeptide with the candidate molecule to result in an Env polypeptide-candidate small molecule mixture; d) measuring the affinity of a cryptic epitope antibody to bind to the Env polypeptide-candidate small molecule mixture formed in step c); and e) based upon the affinity measured in step d), selecting a candidate molecule effective to form an Env polypeptide-candidate small molecule complex whose binding affinity to a cryptic epitope antibody is greater than or equal to a known cryptic epitope antibody antigen.

In one embodiment of the above aspect of the invention, the screening method further includes the step of crosslinking the candidate small molecule to the Env polypeptide to provide a covalently linked Env polypeptide/candidate small molecule complex.

In another embodiment of this aspect, the method further includes the step of comparing the binding affinity of the cryptic epitope antibody and the Env polypeptide/candidate small molecule complex to the binding affinity of the cryptic epitope antibody and the Env polypeptide per se, or to the binding affinity of the cryptic epitope antibody and an Env polypeptide/CD4 polypeptide complex.

Various embodiments of the screening method include those in which the Env polypeptide is a gp120 polypeptide, and/or where the candidate molecule is, for example, a known competitive CD4 inhibitor of a gp120 polypeptide, a known β turn mimetic, or is a member of a small molecule library, wherein the members of the library comprise a fused bicyclic or tricyclic core structure, among others.

In another embodiment of the screening method, the cryptic epitope antibody is bound to a solid support, e.g., one that comprises a gold film surface.

In another aspect, the invention is directed to a method of producing an antibody that binds to a cryptic epitope of an Env polypeptide. In such a method, an immunological composition of the invention is administered to a mammalian subject under conditions effective to form antibodies in the subject.

A further embodiment of the above includes a method that includes the step of isolating the antibodies formed by the subject (for example, neutralizing antibodies, or monoclonal antibodies, or polyclonal antibodies).

Also provided is the use of the Env polypeptide and a small molecule CD4 mimetic having any one or more of the herein described features in the preparation of a medicament for treating or preventing an Env polypeptide-mediated disease.

The following numbered embodiments are encompassed by the present invention:

1. An immunogenic composition comprising an Env polypeptide and a CD4 mimetic, wherein said CD4 mimetic interacts with said Env polypeptide to form an Env polypeptide/CD4 mimetic complex to expose cryptic epitopes on the Env polypeptide/CD4 mimetic complex.
2. The immunogenic composition of Embodiment 1, wherein the binding affinity of a cryptic epitope antibody to said Env polypeptide/CD4 mimetic complex is greater than the binding affinity of said cryptic epitope antibody to said Env polypeptide alone.
3. The immunogenic composition of Embodiment 2, wherein said cryptic epitope antibody is MAbs 17b or 48D.
4. The immunogenic composition of Embodiment 1, wherein said Env polypeptide/CD4 mimetic complex exhibits at least 1% percent upregulation of the 17b epitope compared to the Env polypeptide alone.
5. The immunogenic composition of Embodiment 1, wherein said Env polypeptide is a gp120 polypeptide.
6. The immunogenic composition of Embodiment 1, wherein said CD4 mimetic is a peptoid.
7. The immunogenic composition of Embodiment 6, wherein said peptoid has a molecular weight of less than about 2000 daltons.
8. The immunogenic composition of Embodiment 7, wherein said peptoid is further conjugated to a small molecule to form a peptoid-small molecule conjugate.
9. The immunogenic composition of Embodiment 8, wherein said peptoid small molecule conjugate is crosslinked to said Env polypeptide, to form a covalently crosslinked Env polypeptide/CD4 mimetic complex.
10. The immunogenic composition of Embodiment 1, wherein said CD4 mimetic is a small molecule having a molecular weight of less than about 1000 daltons.
11. The immunogenic composition of Embodiment 10, wherein said small molecule is crosslinked to said Env polypeptide, to form a covalently bound Env polypeptide/CD4 mimetic complex.
12. The immunogenic composition of Embodiment 10, wherein said small molecule is a competitive CD4 inhibitor of a gp120 polypeptide.
13. The immunogenic composition of Embodiment 1, wherein said CD4 mimetic corresponds to one of Structures I, II, or III, including stereoisomers and salts thereof:

where in each of structures I, II and III:

W, X, Y, and Z are each independently selected from the group consisting of carbon and nitrogen, provided that no more than one of W, X, Y, or Z is nitrogen;

$R_1, R_1', R_2, R_3, R_4, R_5$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, halogen, CN, phenyl, nitro, $OC(O)R_{15}$, $C(O)R_{15}$, $C(O)OR_{16}$, $C(O)NR_{17}R_{18}$, $OR_{19}$, $SR_{20}$, and $NR_{21}R_{22}$, each of said alkyl and cycloalkyl being optionally substituted with one to three substituents independently selected from halogen, CN, $NO_2$, $OC(O)R_{15}$, $C(O)R_{15}$, $C(O)OR_{15}$, $C(O)NR_{17}R_{18}$, $OR_{19}$, $SR_{20}$, and $NR_{21}R_{22}$, with the proviso that $R_2$, $R_3$, $R_4$, or $R_5$ is absent when the ring atom to which it is attached is a double-bonded nitrogen, i.e., a trivalent nitrogen;

$R_{15}$, is independently selected from the group consisting of H, $C_1$-$C_6$ alkyl, $C_3$-$C_6$ cycloalkyl, $C_2$-$C_6$ alkenyl, and $C_4$-$C_6$ cycloalkenyl;

$R_{16}$, $R_{19}$, and $R_{20}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_3$-$C_6$ alkynyl, phenyl, and benzyl, wherein each of said alkyl, cycloalkyl, phenyl, and benzyl are optionally substituted with one, two, or three substituents selected from the group consisting of halogen, $NR_{21}R_{22}$, OH, CN, or $NO_2$; provided the carbon atoms that comprise the carbon-carbon triple bond of said $C_3$-$C_6$ alkynyl are not the point of attachment to the oxygen or sulfur to which $R_{16}$, $R_{19}$, or $R_{20}$ is attached;

$R_{17}$ and $R_{18}$ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl, wherein each of said alkyl and cycloalkyl are optionally substituted with one, two, or three substituents selected from the group consisting of halogen, $NR_{21}R_{22}$, OH, CN, or $NO_2$; provided the carbon atoms that comprise the carbon-carbon double bond of said $C_3$-$C_6$ alkenyl or the carbon-carbon triple bond of said $C_3$-$C_6$ alkynyl are not the point of attachment to the nitrogen to which $R_{17}$ and $R_{18}$ is attached;

$R_{21}$ and $R_{22}$ are each independently selected from the group consisting of H, OH, $C_1$-$C_6$ alkyl, $C_3$-$C_6$ cycloalkyl, $C_3$-$C_6$ alkenyl, $C_5$-$C_6$ cycloalkenyl, $C_3$-$C_6$ alkynyl, phenyl, and $C(O)R_{23}$; provided the carbon atoms that comprise the carbon-carbon double bond of said $C_3$-$C_6$ alkenyl, $C_4$-$C_6$ cycloalkenyl, or the carbon-carbon triple bond of said $C_3$-$C_6$ alkynyl are not the point of attachment to the nitrogen to which $R_{21}$ and $R_{22}$ is attached;

$R_{23}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_2$-$C_6$ alkynyl;

$R_6$ is $(CH_2)_nQ$, wherein n is 0-6;

Q is selected from:
(1) H, $C_1$-$C_6$ alkyl, $C_3$-$C_6$ cycloalkyl, $C_2$-$C_6$ alkenyl, $C_4$-$C_6$ cycloalkenyl, $C_3$-$C_6$ alkynyl, halogen, CN, Ar, $NO_2$, $C(O)R_{24}$, $C(O)OR_{25}$, $C(O)NR_{26}R_{27}$, COOAr, $TR_6$, $NR_{21}R_{22}$, $NC(O)NR_{21}R_{22}$, $OC(O)R_{16}$, $(N(R_{21})_2)C=N$-$T$-$R_{22}$, $C(O)Ar$, or $S(O)_mR_{21}$;
(2) a 4-7 membered heterocyclic ring, optionally substituted with $R_{16}$, which may contain 1-3 heteroatoms selected from the group consisting of O, S, SO, $SO_2$, N, and $NR_{24}$;

T is S or O;

m is 0-2;

$R_{24}$ is selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl;

$R_{25}$ is selected from the group consisting of $C_1$-$C_6$ alkyl, $C_3$-$C_6$ cycloalkyl, $C_2$-$C_6$ alkenyl, $C_4$-$C_6$ cycloalkenyl, and $C_3$-$C_6$ alkynyl; provided the carbon atoms that comprise the carbon-carbon triple bond of said $C_3$-$C_6$ alkynyl are not the point of attachment to the oxygen to which $R_{25}$ is attached;

$R_{26}$ and $R_{27}$ are each independently selected from the group consisting of H, $C_1$-$C_6$ alkyl, $C_3$-$C_6$ cycloalkyl, $C_3$-$C_6$ alkenyl, $C_5$-$C_6$ cycloalkenyl, and $C_3$-$C_6$ alkynyl; provided the carbon atoms that comprise the carbon-carbon double bond of said $C_3$-$C_6$ alkenyl, $C_5$-$C_6$ cycloalkenyl, or the carbon-carbon triple bond of said $C_3$-$C_6$ alkynyl are not the point of attachment to the nitrogen to which $R_{26}$ and $R_{27}$ are attached;

$R_7$, $R_8$, $R_9$, $R_{10}$, $R_{11}$, $R_{12}$, $R_{13}$, and $R_{14}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, $CR_{28}R_{29}OR_{30}$, $C(O)R_{31}$, $CR_{32}(OR_{33})OR_{34}$, $CR_{35}NR_{36}R_{37}$, $C(O)OR_{38}$, $C(O)NR_{39}R_{40}$, $CR_{41}R_{42}F$, $CR_{43}F_2$, and $CF_3$, each of said alkyl and cycloalkyl being optionally substituted with one to three substituents independently selected from halogen, CN, $NO_2$, $OC(O)R_{15}$, $C(O)R_{15}$, $C(O)OR_{15}$, $C(O)NR_{17}R_{18}$, $OR_{19}$, $SR_{20}$, and $NR_{21}R_{22}$, or $R_8$ and $R_9$ may be absent such that the carbon ring atoms to which each is independently attached together form a double bond.

$R_{28}$, $R_{29}$, $R_{30}$, $R_{31}$, $R_{32}$, $R_{35}$, $R_{41}$, $R_{42}$ and $R_{43}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, and $C(O)R_{44}$;

$R_{33}$, $R_{34}$ and $R_{38}$ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl; provided the carbon atoms that comprise the carbon-carbon triple bond of said $C_3$-$C_6$ alkynyl are not the point of attachment to the oxygen to which $R_{34}$ and $R_{38}$ are attached;

$R_{36}$ and $R_{37}$ are each independently selected from the group consisting of H, $C_1$-$C_6$ alkyl, $C_1$-$C_6$ cycloalkyl, $C_3$-$C_6$ alkenyl, $C_4$-$C_6$ cycloalkenyl, and $C_3$-$C_6$ alkynyl; provided the carbon atoms that comprise the carbon-carbon triple bond of said $C_3$-$C_6$ alkynyl are not the point of attachment to the nitrogen to which $R_{36}$ and $R_{37}$ are attached;

$R_{39}$ and $R_{40}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_3$-$C_6$ alkynyl; provided the carbon atoms that comprise the carbon-carbon triple bond of said $C_3$-$C_6$ alkynyl are not the point of attachment to the nitrogen to which $R_{39}$ and $R_{40}$ are attached; $R_{44}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_2$-$C_6$ alkynyl;

J is —(CO)—, —(CO)$CH_2$—, —(CO)(CO)—, or —(CO)$CHR_9$—;

U is nitrogen or CH;

L is —(CO)— or —$CH_2$—;

$R_A$, $R_B$, and $R_C$ are independently selected from the group consisting of Ar, H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, halogen, CN, nitro, $OC(O)R_{15}$, $C(O)R_{15}$, $C(O)OR_{16}$, $C(O)NR_{17}R_{18}$, $OR_{19}$, $SR_{20}$ and $NR_{21}R_{22}$, each of said alkyl and cycloalkyl being optionally substituted with one to three substituents independently selected from halogen, CN, $NO_2$, $OC(O)R_{15}$, $C(O)R_{15}$, $C(O)OR_{15}$, $C(O)NR_{17}R_{18}$, $OR_{19}$, $SR_{20}$, and $NR_{21}R_{22}$;

Ar is a 5-12 membered aromatic ring optionally containing one to five heteroatoms independently selected from the group consisting of O, S, N, or $NR_{16}$ and optionally substituted with one to six substitutents independently selected from the group consisting of $R_{45}$, $R_{46}$, $R_{47}$, $R_{48}$, or $R_{49}$;

$R_{45}$ $R_{46}$, $R_{47}$, $R_{48}$, and $R_{49}$ are each independently H, $C_1$-$C_6$ alkyl, $C_3$-$C_6$ cycloalkyl, $C_2$-$C_6$ alkenyl, $C_3$-$C_6$ cycloalkenyl, $C_2$-$C_6$ alkynyl, halogen, CN, nitro, $C(O)R_{45}$, $COOR_{46}$, hydroxyl, hydroxymethyl, trifluoromethyl, trifluoromethoxy, O-benzyl, O-phenyl, $OC(O)C_1$-$C_6$ alkyl, $SC(O)C_1$-$C_6$ alkyl, $S(O)_mC_1$-$C_6$ alkyl, $S(O)_2 NR_{21}R_{22}$, O—V, $CH_2$ $(CH_2)_p$—V, $O(CH_2)$——V, $(CH_2)_pO$—V, CH=CH—V, or $TR_{47}$, each of said alkyl and cycloalkyl being optionally substituted with one to three substitutents independently selected from the group consisting of, $NR_{21}NR_{22}$, OH, CN, or $NO_2$;

V is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl;

p is 1-2;

$R_{45}$ and $R_{46}$ are each independently H, $C_1$-$C_6$ alkyl, or $C_3$-$C_6$ cycloalkyl;

$R_{47}$ is H, $C_1$-$C_6$ alkyl, $C_3$-$C_6$ cycloalkyl, $C_2$-$C_6$ alkenyl, $C_3$-$C_6$ cycloalkenyl, $C_2$-$C_6$ alkynyl, $C(O)R_{48}$ or $C(O)OR_{49}$, each of said alkyl and cycloalkyl being optionally substituted with one to three substitutents independently selected from the group consisting of, $NR_{21}NR_{22}$, OH, CN, or $NO_2$; and $R_{48}$, $R_{49}$ are each independently H, $C_1$-$C_6$ alkyl, or $C_3$-$C_6$ cycloalkyl, each of said alkyl and cycloalkyl being optionally substituted with one to three substitutents independently selected from the group consisting of, $NR_{21}NR_{22}$, OH, CN, or $NO_2$, provided that said compound is not 1-[4-(methyloxy)-1H-pyrrolo[2,3-b]pyridin-3-yl]-2-[(2R)-2-methyl-4-(phenylcarbonyl)piperazin-1-yl]-2-oxoethanone, 1-[4,7-bis(methyloxy)-1H-indol-3-yl]-2-oxo-2-[4-(phenylcarbonyl)piperazin-1-yl]ethanone, or 1-(1H-indol-3-yl)-2-oxo-2-[4-(phenylcarbonyl)piperazin-1-yl]ethanone.

14. The immunogenic composition of Embodiment 13, wherein J is —(CO)CH$_2$— or —(CO)CHR$_9$—.

15. The immunogenic composition of Embodiment 13, wherein J is —(CO)—.

16. The immunogenic composition of Embodiment 13, wherein U is nitrogen and L is —CH$_2$—.

17. The immunogenic composition of Embodiment 13, wherein U is nitrogen and L is —(CO)—.

18. The immunogenic composition of Embodiment 13, wherein W, X, Y, and Z are carbon.

19. The immunogenic composition of Embodiment 13, wherein n is 0 and Q is H or C$_1$-C$_6$ alkyl.

20. The immunogenic composition of Embodiment 13, wherein R$_A$, R$_B$, and R$_C$ are independently selected from the group consisting of Ar, C(O)OR$_{16}$, and NR$_{21}$R$_{22}$.

21. The immunogenic composition of Embodiment 13, wherein Ar is selected from the group consisting of wherein:

A$_1$, A$_2$, A$_3$, A$_4$, A$_5$, B$_1$, B$_2$, B$_3$, B$_4$, C$_1$, C$_2$, C$_3$, D$_1$, D$_2$, and D$_3$ are each independently selected from the group consisting of H, CN, halogen, NO$_2$, C$_1$-C$_6$ alkyl, C$_3$-C$_6$ cycloalkyl, C$_2$-C$_6$ alkenyl, C$_4$-C$_6$ cycloalkenyl, C$_2$-C$_6$ alkynyl, OR$_{50}$, NR$_{51}$R$_{52}$, SR$_{53}$, N$_3$, and CH(—N=N—)CF$_3$;

R$_{50}$ is selected from the group consisting of H, C$_1$-C$_6$ alkyl, C$_3$-C$_6$ cycloalkyl, C$_2$-C$_6$ alkenyl, C$_4$-C$_6$ cycloalkenyl, and C$_3$-C$_6$ alkynyl; provided the carbon atoms that comprise the carbon-carbon triple bond of said C$_3$-C$_6$ alkynyl are not the point of attachment to the oxygen to which R$_{50}$ is attached;

R$_{51}$ and R$_{52}$ are each independently selected from the group consisting of H, C$_1$-C$_6$ alkyl, C$_3$-C$_6$ cycloalkyl, C$_3$-C$_6$ alkenyl, C$_5$-C$_6$ cycloalkenyl, C$_3$-C$_6$ alkynyl, and C(O)R$_{55}$; provided the carbon atoms that comprise the carbon-carbon double bond of said C$_5$-C$_6$ alkenyl, C$_4$-C$_6$ cycloalkenyl, or the carbon-carbon triple bond of said C$_3$-C$_6$ alkynyl are not the point of attachment to the nitrogen to which R$_{51}$ and R$_{52}$ are attached;

R$_{53}$ is selected from the group consisting of H, C$_1$-C$_6$ alkyl, C$_3$-C$_6$ cycloalkyl, C$_2$-C$_6$ alkenyl, C$_4$-C$_6$ cycloalkenyl, C$_3$-C$_6$ alkynyl and C(O)R$_{54}$; provided the carbon atoms that comprise the carbon-carbon triple bond of said C$_3$-C$_6$ alkynyl are not the point of attachment to the sulfur to which R$_{53}$ is attached;

R$_{54}$ is C$_1$-C$_6$ alkyl or C$_3$-C$_6$ cycloalkyl; and

R$_{55}$ is selected from the group consisting of H, C$_1$-C$_6$ alkyl, and C$_3$-C$_6$ cycloalkyl.

22. The immunogenic composition of Embodiment 13, wherein said CD4 mimetic is selected from the group consisting of 1-[2-(5-methoxy-1H-indol-3-yl)-2-oxoethyl]piperidine-4-carboxamide, 2-(4-benzylpiperazin-1-yl)-1-(5-methoxy-1H-indol-3-yl)ethanone, {1-[(4,6-dimethyl-1H-indol-2-yl)carbonyl]piperidin-4-yl}(4-fluorophenyl)methanone, 1-[2-(5-methoxy-1,2-dimethyl-1H-indol-3-yl)-1-methyl-2-oxoethyl]piperidine-4-carboxamide, ethyl-1-[(4,6-dimethyl-1H-indol-2-yl)carbonyl]piperidine-4-carboxylate, 6-{[4-(2,6-difluorobenzoyl)piperazin-1-yl]carbonyl}-1H-indole, 2-{[4-(1H-indol-6-ylcarbonyl)piperazin-1-yl]carbonyl}phenyl acetate, 6-{[4-(3,4,5-trimethoxybenzoyl)piperazin-1-yl]carbonyl}-1H-indole, 1-[2-(5-methoxy-1,2-dimethyl-1H-indol-3-yl)-2-oxoethyl]piperidine-4-carboxamide, and 4-{[4-(2-furoyl)piperazin-1-yl]carbonyl}-9H-fluoren-9-one.

23. The immunogenic composition of Embodiment 1, further comprising an adjuvant.

24. A method of eliciting an immune response in a subject, the method comprising administering an Env polypeptide and a CD4 mimetic to said subject, wherein said CD4 mimetic interacts with said Env polypeptide to expose cryptic epitopes on an Env polypeptide/CD4 mimetic complex.

25. The method of Embodiment 24, wherein said Env polypeptide and said CD4 mimetic are administered intramuscularly or subcutaneously.

26. The method of Embodiment 24, wherein the exposed cryptic epitope is CD4i.

27. The method of Embodiment 24, wherein said immune response is the cellular production of antibodies to CD4i.

28. The method of Embodiment 24, wherein said Env polypeptide is a gp120 polypeptide.

29. The method of Embodiment 24, wherein said CD4 mimetic is a CD4 mimetic according to any one of embodiments 5-21.

30. A method of identifying a CD4 mimetic capable of interacting with an Env polypeptide to expose cryptic epitopes on said Env polypeptide, the method comprising the steps of:
    a) providing an Env polypeptide;
    b) providing a compound;
    c) contacting said Env polypeptide with said compound;
    d) measuring the affinity of a cryptic epitope antibody to bind to an Env polypeptide/compound complex; and
    e) selecting said compound.

31. The method of Embodiment 30, further comprising the step of crosslinking said compound to said Env polypeptide to provide a covalently linked Env polypeptide/compound complex.

32. The method of Embodiment 30, further comprising the step of comparing the binding affinity of said cryptic epitope antibody and said Env polypeptide/compound complex to
    a) the binding affinity of said cryptic epitope antibody and the Env polypeptide, or to
    b) the binding affinity of said cryptic epitope antibody and an Env polypeptide/CD4 polypeptide complex.

33. The method of Embodiment 30, wherein said Env polypeptide is a gp120 polypeptide.

34. The method of Embodiment 30, wherein said compound is a known competitive CD4 inhibitor of a gp120 polypeptide.

35. The method of Embodiment 30, wherein said compound is a known β turn mimetic.

36. The method of Embodiment 30, wherein said compound is a member of a small molecule or peptoid library.

37. The method of Embodiment 30, wherein said cryptic epitope antibody is selected from the group consisting of MAbs 17b and 48D.

38. The method of Embodiment 30, wherein said cryptic epitope antibody is bound to a solid support.
39. The method of Embodiment 38, wherein the surface of said solid support comprises a gold film.
40. A method of producing antibodies that bind to cryptic epitopes of an Env polypeptide, the methods comprising the step of:
   a) administering an immunological composition according to any of Embodiments 1-22 to a subject under conditions that allow production of antibodies in the subject.
41. The method of Embodiment 40, further comprising the step of isolating the antibodies produced in the subject.
42. The method of Embodiments 40 or 41, wherein the antibodies are neutralizing antibodies.
43. The method of Embodiments 40, 41, and 42, wherein the antibodies are monoclonal antibodies.
44. The method of Embodiments 40, 41, and 42, wherein the antibodies are polyclonal antibodies.
45. Use of the Env polypeptide and the CD4 mimetic of any one of Embodiments 5-22 in the preparation of a medicament for treating or preventing an Env polypeptide mediated disease.

In another aspect, the invention includes complexes of any HIV Env polypeptide and any of the small molecule CD4 mimetics described herein. In certain embodiments, the HIV Env polypeptide is based on strain SMF162. In certain embodiments, the HIV Env polypeptide comprises one or more amino acid deletions in V1, V2, V3, V4 and/or V5. In yet another embodiment, the polypeptide comprises an HIV Env polypeptide (e.g., native or modified gp160, gp140, oligomeric-gp140, gp120) complexed to a CD4 mimetic. The HIV Env polypeptide and CD4 protein can be complexed by crosslinking (e.g., using formaldehyde); using a fixative (e.g., formalin); and/or can complex spontaneously under suitable conditions.

In another aspect, the invention includes a method of producing antibodies that bind to cryptic epitopes of HIV Env, the methods comprising the step of administering any of the CD4 mimetics described herein to a subject under conditions that allow production of antibodies (e.g., neutralizing antibodies, monoclonal antibodies, polyclonal antibodies) in the subject. In certain embodiments, the antibodies produced by the subject are then isolated.

In another aspect, the invention includes immunogenic compositions comprising any of the mimetics, complexes and/or antibodies described herein. In certain embodiments, the immunogenic compositions further comprise one or more adjuvants.

In yet another aspect, the invention includes a method of inducing an immune response (e.g., a humoral response such as a neutralizing antibody response and/or a cellular immune response) in subject comprising, administering any of the mimetics and/or complexes described herein to a subject in an amount sufficient to induce an immune response in the subject.

In certain embodiments, the method comprises (a) administering a first composition comprising any of the mimetics, complexes and/or antibodies described herein in a priming step and (b) administering a second composition comprising any of the mimetics, complexes and/or antibodies described herein, as a booster, in an amount sufficient to induce an immune response in the subject.

In any of the methods described herein, the subject can be a mammal, for example a human or non-human mammal and the introduction can be intramuscularly, intramucosally, intranasally, subcutaneously, intradermally, transdermally, intravaginally, intrarectally, orally and/or intravenously.

These and other embodiments of the subject invention will readily occur to those of skill in the art in light of the disclosure herein.

Each and every feature of the invention described herein is meant to apply equally to each and every embodiment of the invention even if not explicitly stated.

BRIEF DESCRIPTION OF THE DRAWINGS

FIG. 3 is a table containing a compilation of screening data for representative small molecule CD4 mimetics in accordance with the invention as described in detail in Example 6;

DETAILED DESCRIPTION

Figure 1:
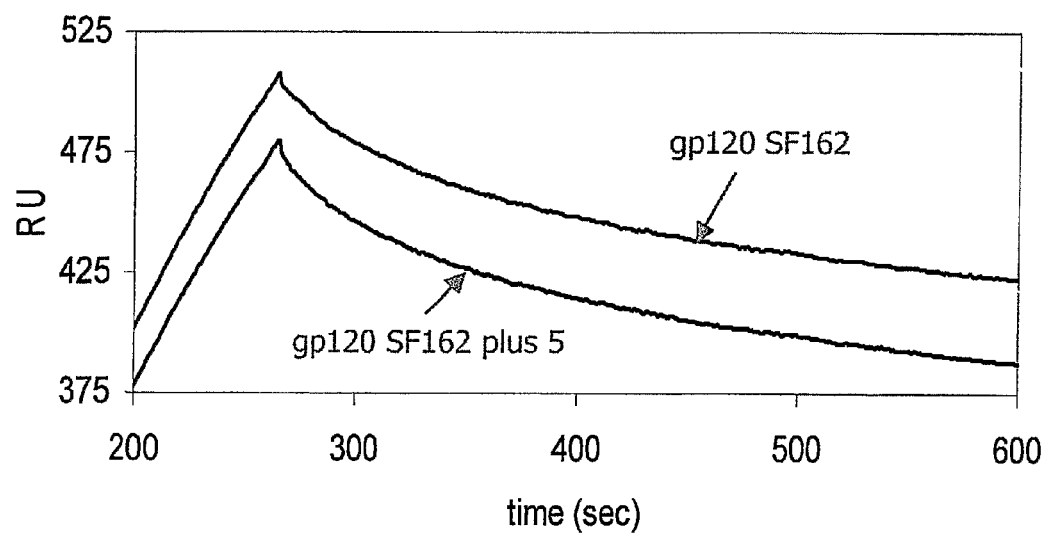
FIG. 1 is a graph depicting inhibition of CD4 binding to Env upon binding of a representative CD4 mimetic of the invention, ethyl 1-[(4,6-dimethyl-1H-indol-2-yl)carbonyl]piperidine-4-carboxylate, 5, as determined by surface plasmon resonance (SPR) analysis (Example 1)

The practice of the present invention will employ, unless otherwise indicated, conventional methods of chemistry, viral immunobiology, molecular biology and recombinant DNA techniques within the skill of the art. Such techniques are explained fully in the literature. See, e.g., T. E. Creighton, *Proteins: Structures and Molecular Properties* (W.H. Freeman and Company, 1993); Nelson L. M. and Jerome H. K. *HIV Protocols* in Methods in Molecular Medicine, vol. 17, 1999; Sambrook, et al., *Molecular Cloning: A Laboratory Manual* (Cold Spring Harbor Laboratory, 1989); F. M. Ausubel et al. *Current Protocols in Molecular Biology*, Greene Publishing Associates & Wiley Interscience New York; and Lipkowitz and Boyd, *Reviews in Computational Chemistry*, volumes 1-present (Wiley-VCH, New York, N.Y., 1999).

It must be noted that, as used in this specification and the appended claims, the singular forms "a", "an" and "the" include plural referents unless the content clearly dictates otherwise. Thus, for example, reference to "a CD4 mimetic" includes a mixture of two or more mimetics, and the like.

All publications, patents and patent applications cited herein, whether supra or infra, are hereby incorporated by reference in their entirety.

Definitions

In describing the present invention, the following terms will be employed, and are intended to be defined as indicated below.

The term "CD4 mimetic" refers to a molecule that interacts with an Env polypeptide (e.g., gp120, gp140, gp160), preferably such that functional epitopes (e.g., cryptic epitopes) in or near the CD4 and/or chemokine receptor binding sites(s) are exposed. Cryptic epitopes are also referred to herein as inducible epitopes.

The term "small molecule" refers to an organic compound either synthesized in the laboratory or found in nature. Typically, a small molecule is characterized in that it contains several carbon-carbon bonds, and has a molecular weight of less than 2500, preferably less than 2000, even more preferably less than about 1500, still more preferably less than about 1500, even more preferably less than about 1000, and most preferably less than about 750. A small molecule is non-macromolecular in nature, that is to say, does not contain a multiple repetitions (e.g., more than 5 repeat units) of a particular type of monomer subunit, such as in the case of macromolecules such as proteins, and other polymers. Examples of "small molecules" that occur in nature include, but are not limited to, taxol, dynemicin, and rapamycin. Examples of "small molecules" that are synthesized in the laboratory include, but are not limited to, the CD4 mimetics described herein. Small molecules may be readily prepared by synthetic organic techniques, such as by combinatorial chemistry techniques. See, e.g., U.S. Pat. No. 6,448,443. A small molecule CD4 mimetic in accordance with the invention excludes the following: 1-[4-(methyloxy)-1H-pyrrolo[2,3-b]pyridin-3-yl]-2-[(2R)-2-methyl-4-(phenylcarbonyl)piperazin-1-yl]-2-oxoethanone, 1-[4,7-bis(methyloxy)-1H-indol-3-yl]-2-oxo-2-[4-(phenylcarbonyl)piperazin-1-yl]ethanone, and 1-(1H-indol-3-yl)-2oxo-2-[4-(phenylcarbonyl)piperazin-1-yl]ethanone.

The term "acylamino" as used herein refers to an acyl (CO—) radical to which an amino group is appended.

The term "loweralkyl" as used herein refers to branched or straight chain acyclical alkyl groups comprising one to ten carbon atoms, including, e.g., methyl, ethyl, propyl, isopropyl, n-butyl, t-butyl, neopentyl and the like.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following that are provided by way of example: —CH($CH_3$)$_2$, —CH($CH_3$)($CH_2CH_3$), —CH($CH_2CH_3$)$_2$, —C($CH_3$)$_3$, —C($CH_2CH_3$)$_3$, —$CH_2$CH($CH_3$)$_2$, —$CH_2$CH($CH_3$)($CH_2CH_3$), —$CH_2$ CH($CH_2CH_3$)$_2$, —$CH_2$C($CH_3$)$_3$, —$CH_2$C($CH_2CH_3$)$_3$, —CH($CH_3$)CH($CH_3$)($CH_2CH_3$), —$CH_2CH_2$CH($CH_3$)$_2$, —$CH_2CH_2$ CH($CH_3$)($CH_2CH_3$), —$CH_2CH_2$CH($CH_2CH_3$)$_2$, —$CH_2CH_2$C($CH_3$)$_3$, —$CH_2CH_2$C($CH_2CH_3$)$_3$, —CH($CH_3$)$CH_2$CH($CH_3$)$_2$, —CH ($CH_3$)CH($CH_3$)CH($CH_3$)$_2$, —CH ($CH_2CH_3$)CH($CH_3$)CH ($CH_3$)($CH_2CH_3$), and others. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 6 carbon atoms. Most preferred unsubstituted alkyl groups include straight and branched chain alkyl groups having from 1 to 3 carbon atoms and include methyl, ethyl, propyl, and —CH($CH_3$)$_2$.

The phrase "cycloalkyl" includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound.

The phrase "cycloalkenyl" includes cyclic alkyl groups containing at least one double bond between two ring carbons such as cyclobutene, and cyclopentene, and cyclohexene. Preferred cycloalkenyl groups have four to six carbon atoms.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; a phosphorus atom in groups such as phosphate and dialkyl alkylphosphonate; oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The term "alkoxy" as used herein refers to RO— wherein R, for example, is alkyl such as lower alkyl defined above. Representative examples of lower alkyl alkoxy groups include methoxy, ethoxy, t-butoxy and the like.

The term "substituted alkoxy" as used herein refers to RO—, where R is, for example, an alkyl substituted, for example, with a halogen. RO is for example $OCF_3$. Another example of substituted alkoxy is arylalkoxy.

The term "alkenyl" as used herein refers to a branched or straight chain groups comprising two to twenty carbon atoms that also comprise one or more carbon-carbon double bonds. Representative alkenyl groups include prenyl, 2-propenyl (i.e., allyl), 3-methyl-2-butenyl, 3,7-dimethyl-2,6-octadienyl, 4,8-dimethyl-3,7-nonadienyl, 3,7,11-trimethyl-2,6,10-dodecatrienyl and the like.

The term "substituted alkenyl" as used herein refers to alkenyl groups that are substituted, for example, diethyl hex-5-enylphosponate, and others with an alkyl or substituted alkyl group such as dialkyl phosphate or an ester such as an acetate ester.

The term "dialkyl amino" as used herein refers to an amino group substituted with two alkyl groups such as C1-20 alkyl groups.

The term "substituted dialkyl amino" as used herein refers to a dialkylamino substituted, for example, with a carboxylic acid, ester, hydroxy or alkoxy.

The term "hydroxyalkylthio" as used herein refers to a thio radical to which is appended a hydroxyalkyl group, where the alkyl is for example lower alkyl. An example is hydroxyethylthio, —SCH$_2$CH$_2$OH.

The term "N-alkylsulfonamide" as used herein refers to the group —SO$_2$NHalkyl, where alkyl is, for example, octyl.

The term "alkynyl" as used herein refers to a branched or straight chain comprising two to twenty carbon atoms that also comprises one or more carbon-carbon triple bonds. Representative alkynyl groups include ethynyl, 2-propynyl (propargyl), 1-propynyl and the like. Preferred alkynyl groups have two to six carbon atoms.

The phrase "aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to aryl groups that substituted alkyl groups had with respect to alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "arylalkylaryl" as used herein refers to an arylalkyl group as previously defined appended to an aryl group. Representative arylalkylaryl groups include 4-benzylphenyl, 3-benzylphenyl, 4-phenethylphenyl and the like.

The term "arylaryl" as used herein refers to an aryl group as previously defined that is appended to an aryl group. Representative arylaryl groups include biphenyl, 4-(1-naphthyl)phenyl, 4-(2-naphthyl)phenyl and the like.

The term "aryloxy" as used herein refers to RO— wherein R is an aryl group. Representative arylalkoxy group include benzyloxy, phenylethoxy and the like.

The term "arylalkoxy" as used herein refers to a lower alkoxy radical to which is appended an aryl group. Representative arylalkoxy group include benzyloxy, phenylethoxy and the like.

The term "aryloxyaryl" as used herein refers to an aryl radical to which is appended an aryloxy group. Representative aryloxyaryl groups include 4-phenoxyphenyl, 3-phenoxyphenyl, 4-phenoxy-1-naphthyl, 3-phenoxy-1-naphthyl and the like.

The term "aryloxyarylalkyl" as used herein refers to an arylalkyl radical to which is appended an aryloxy group. Representative aryloxyarylalkyl groups include 4-phenoxyphenylmethyl, 3-phenoxyphenylmethyl, 4-phenoxyphenylethyl, 3-phenoxyphenylethyl and the like.

The term "arylalkoxyaryl" as used herein refers to an aryl radical to which is appended an arylalkoxy group. Representative arylalkoxyaryl groups include 4-benzyloxylphenyl, 3-benzyloxyphenyl and the like.

The term "arylalkoxyarylalkyl" as used herein refers to an arylalkyl radical to which is appended an arylalkoxy group. Representative arylalkoxyarylalkyl groups include 4-benzyloxylbenzyl, 3-benzyloxybenzyl and the like.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl and the like.

The term "halogen" refers to iodine, bromine, chlorine or fluorine; "halo" as used herein refers to iodo, bromo, chloro or fluoro.

The term "haloalkyl" as used herein refers to a lower alkyl radical, as defined above, bearing at least one halogen substituent, for example, chloromethyl, fluoroethyl or trifluoromethyl and the like.

The phrase "heterocyclyl" refers to both aromatic and non-aromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2 H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, t-butyloxycarbonyl, and 2-chloropyridyl among others.

"Substituted" refers to the definite replacement of hydrogen with one or more monovalent or divalent radicals. Suitable substitution groups include, those described herein for particular groups, as well as hydroxyl, nitro, amino, imino, cyano, halo, thio, thioamido, amidino, imidino, oxo, oxamidino, methoxamidino, imidino, guanidino, sulfonamido, carboxyl, formyl, alkyl, substituted alkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, benzyl, pyridyl, pyrazolyl, pyrrole, thiophene, imidazolyl, and the like.

By overall atom length, e.g., in the context of a linker of the invention, is meant the number of atoms in a single chain, not counting substituents. For instance, —CH$_2$— counts as one atom with respect to overall linker length, —CH$_2$CH$_2$O— counts as 3 atoms in length, and a non-linear group such as a phenyl ring counts as 4 atoms in length.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

The terms "polypeptide," and "protein" are used interchangeably herein to denote any polymer of amino acid residues. The terms encompass peptides, oligopeptides, dimers, multimers, and the like. Such polypeptides can be derived from natural sources or can be synthesized or recombinantly produced. The terms also include postexpression modifications of the polypeptide, for example, glycosylation, acetylation, phosphorylation, etc.

A polypeptide as defined herein is generally made up of the 20 natural amino acids Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y) and Val (V) and may also include any of the several known amino acid analogs, both naturally occurring and synthesized analogs, such as but not limited to homoisoleucine, asaleucine, 2-(methylenecyclopropyl)glycine, S-methylcysteine, S-(prop-1-enyl)cysteine, homoserine, ornithine, norleucine, norvaline, homoarginine, 3-(3-carboxyphenyl)alanine, cyclohexylalanine, mimosine, pipecolic acid, 4-methylglutamic acid, canavanine, 2,3-diaminopropionic acid, and the like. Further examples of polypeptide agents that will find use in the present invention are set forth below.

By "geometry" or "tertiary structure" of a polypeptide or protein is meant the overall 3-D configuration of the protein. As described herein, the geometry can be determined, for example, by crystallography studies or by using various programs or algorithms that predict the geometry based on interactions between the amino acids making up the primary and secondary structures.

By "wild type" or "native" polypeptide, polypeptide agent or polypeptide drug, is meant a naturally occurring polypeptide sequence, and its corresponding secondary structure. An "isolated" or "purified" protein or polypeptide is a protein that is separate and discrete from a whole organism with which the protein is normally associated in nature. It is apparent that the term denotes proteins of various levels of purity. Typically, a composition containing a purified protein will be one in which at least about 35%, preferably at least about 40-50%, more preferably, at least about 75-85%, and most preferably at least about 90% or more, of the total protein in the composition will be the protein in question.

By "Env polypeptide" is meant a molecule derived from an envelope protein, preferably from HIV Env. The envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides. Env polypeptides can exist as monomers, dimers or multimers.

By a "gp120 polypeptide" is meant a molecule derived from a gp120 region of the Env polypeptide. Preferably, the gp120 polypeptide is derived from HIV Env. The primary amino acid sequence of gp120 is approximately 511 amino acids, with a polypeptide core of about 60,000 Daltons. The polypeptide is extensively modified by N-linked glycosylation to increase the apparent molecular weight of the molecule to 120,000 Daltons. The amino acid sequence of gp120 contains five relatively conserved domains interspersed with five hypervariable domains. The positions of the 18 cysteine residues in the gp120 primary sequence of the HIV-1$_{HXB-2}$ (hereinafter "HXB-2") strain, and the positions of 13 of the approximately 24 N-linked glycosylation sites in the gp120 sequence are common to most, if not all, gp120 sequences. The hypervariable domains contain extensive amino acid substitutions, insertions and deletions. Despite this variation, most, if not all, gp120 sequences preserve the virus's ability to bind to the viral receptor CD4. A "gp120 polypeptide" includes both single subunits and/or multimers.

Env polypeptides (e.g., gp120, gp140 and gp160) include a "bridging sheet" comprised of 4 anti-parallel β-strands (β-2, β-3, β-20 and β-21) that form a β-sheet. Extruding from one pair of the β-strands (β-2 and β-3) are two loops, V1 and V2. The β-2 sheet occurs at approximately amino acid residue 119 (Cys) to amino acid residue 123 (Thr) while β-3 occurs at approximately amino acid residue 199 (Ser) to amino acid residue 201 (Ile), relative to HXB-2. The "V1/V2 region" occurs at approximately amino acid positions 126 (Cys) to residue 196 (Cys), relative to HXB-2. (see, e.g., Wyatt et al. (1995) *J. Virol.* 69:5723-5733; Stamatatos et al. (1998) *J. Virol* 72:7840-7845). Extruding from the second pair of β-strands (β-20 and β-21) is a "small-loop" structure, also referred to herein as "the bridging sheet small loop." In HXB-2, β-20 extends from about amino acid residue 422 (Gln) to amino acid residue 426 (Met) while β-21 extends from about amino acid residue 430 (Val) to amino acid residue 435 (Tyr). In variant SMF162, the Met-426 is an Arg (R) residue. The "small loop" extends from about amino acid residue 427 (Trp) through 429 (Lys), relative to HXB-2. Alignment of the amino acid sequences of Env polypeptide gp160 of any HIV variant can be determined relative to other variants, such as HXB-2, as described for example, in WO 00/39303.

Furthermore, an "Env polypeptide" or "gp120 polypeptide" as defined herein is not limited to a polypeptide having the exact sequence described herein. Indeed, the HIV genome is in a state of constant flux and contains several variable domains that exhibit relatively high degrees of variability between isolates. It is readily apparent that the terms encompass Env (e.g., gp120) polypeptides from any of the identified HIV isolates, as well as newly identified isolates, and subtypes of these isolates. Descriptions of structural features are given herein with reference to HXB-2. One of ordinary skill in the art in view of the teachings of the present disclosure and the art can determine corresponding regions in other HIV variants (e.g., isolates HIV$_{IIIb}$, HIV$_{SF2}$, HIV-1$_{SF162}$, HIV-1$_{SF170}$, HIV$_{LAV}$, HIV$_{LAI}$, HIV$_{MN}$, HIV-1$_{CM235}$, HIV-1$_{US4}$, other HIV-1 strains from diverse subtypes (e.g., subtypes, A through G, and O), HIV-2 strains and diverse subtypes (e.g., HIV-2$_{UC1}$ and HIV-2$_{UC2}$), and simian immunodeficiency virus (SIV). (See, e.g., Virology, 3rd Edition (W. K. Joklik ed. 1988); *Fundamental Virology,* 2nd Edition (B. N. Fields and D. M. Knipe, eds. 1991); *Virology,* 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify β-sheet regions). The actual amino acid sequences of the modified Env polypeptides can be based on any HIV variant.

Additionally, the term "Env polypeptide" (e.g., "gp120 polypeptide") encompasses proteins that include additional modifications to the native sequence, such as additional internal deletions, additions and substitutions. These modifications may be deliberate, as through site-directed mutagenesis, or may be accidental, such as through naturally occurring mutational events. Thus, for example, if the Env polypeptide is to be used in vaccine compositions, the modifications must be such that immunological activity (i.e., the ability to elicit an antibody response to the polypeptide) is not lost. Similarly, if the polypeptides are to be used for diagnostic purposes, such capability must be retained.

The term "modified Env polypeptide" is an Env polypeptide (e.g., gp120 as defined above) refers to an Env polypeptide that has been complexed to a CD4 mimetic. The Env polypeptide may optionally be modified in other ways, for example in the variable regions V1 and V2. The Env polypeptide may be monomeric or oligomeric. Generally, complexed Env (e.g., gp120) polypeptides result in exposure of epitopes in or near the CD4 binding site, while allowing correct folding (e.g., correct geometry) of the Env polypeptide. Additionally, modifications (e.g., truncations) to the V1 and V2 loop regions may also be made. Although not all possible V1/V2 modifications have been exemplified herein, it is to be understood that other disrupting modifications are also encompassed by the present invention.

By "binding" is meant the ability of a CD4 mimetic (e.g., peptoid, small molecule, peptoid small molecule conjugate) to specifically interact with an Env polypeptide such that interaction results in a conformational change in the Env polypeptide that leads to exposure of Env epitopes to which neutralizing antibodies are more readily generated.

A polypeptide (e.g., gp120 or other Env polypeptide) is produced "intracellularly" when it is found within the cell, either associated with components of the cell, such as in association with the endoplasmic reticulum (ER) or the Golgi Apparatus, or when it is present in the soluble cellular fraction. The gp120 and other Env polypeptides of the present invention may also be secreted into growth medium so long as sufficient amounts of the polypeptides remain present within the cell such that they can be purified from cell lysates using techniques described herein.

An "immunogenic" gp120 or other Env protein is a molecule that includes at least one epitope such that the molecule is capable of either eliciting an immunological reaction in an individual to which the protein is administered or, in the diagnostic context, is capable of reacting with antibodies directed against the HIV in question.

By "epitope" is meant a site on an antigen to which specific B cells and/or T cells respond, rendering the molecule including such an epitope capable of eliciting an immunological reaction or capable of reacting with HIV antibodies present in a biological sample. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8-10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology. See, also, Geysen et al., *Proc. Natl. Acad. Sci. USA* (1984) 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709-715 (technique for identifying peptides with high affinity for a given antibody). Antibodies that recognize the same epitope can be identified in a simple immunoassay showing the ability of one antibody to block the binding of another antibody to a target antigen. A "cryptic epitope" refers generally to an epitope that is exposed only in certain conformations of the protein.

A "functional epitope" refers to an epitope that elicits antibody which prevents or limits HIV infection. In a particular embodiment, the antibodies are neutralizing antibodies. In other embodiments, the antibodies can, e.g., elicit an ADCC response.

An "immunological response" or "immune response" as used herein can induce the development in the subject of a humoral and/or a cellular immune response to the Env (e.g., gp120) polypeptide when the polypeptide is present in a vaccine composition. Antibodies elicited in an immune response may also neutralize infectivity, and/or mediate antibody-complement or antibody dependent cell cytotoxicity to provide protection to an immunized host. Immunological reactivity may be determined in standard immunoassays, such as a competition assays, well known in the art.

The term "antibody" as used herein includes antibodies obtained from both polyclonal and monoclonal preparations, as well as, the following: (i) hybrid (chimeric) antibody (molecules (see, for example, Winter et al. (1991) Nature 349:293-299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659-2662; and Ehrlich et al. (1980) Biochem 19:4091-4096); (iv) single-chain Fv molecules (sFv) (see, for example, Huston et al. (1988) Proc. Natl. Acad. Sci. USA 85:5879-5883); (v) dimeric and trimeric antibody fragment constructs; (vi) humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579-1584; Cumber et al. (1992) J. Immunology 149B:120-126); (vii) human antibodies; and, (viii) any functional fragments obtained from such molecules, wherein such fragments retain specific-binding properties of the parent antibody molecule.

Thus, the term "antibody" refers to a polypeptide or group of polypeptides that comprise at least one antigen-binding site. An "antigen binding site" is formed from the folding of the variable domains of an antibody molecule(s) to form three-dimensional binding sites with an internal surface shape and charge distribution complementary to the features of an epitope of an antigen, which allows specific binding to form an antibody-antigen complex. An antigen-binding site may be formed from a heavy- and/or light-chain domain (VH and VL, respectively), which form hypervariable loops that contribute to antigen binding. The term "antibody" includes, without limitation, polyclonal antibodies, monoclonal antibodies, chimeric antibodies, altered antibodies, univalent antibodies, Fab proteins, and single-domain antibodies. In many cases, the binding phenomena of antibodies to antigens is equivalent to other ligand/anti-ligand binding.

If polyclonal antibodies are desired, a selected mammal (e.g., mouse, rabbit, goat, horse, etc.) is immunized with an immunogenic polypeptide bearing an HCV epitope(s). Serum from the immunized animal is collected and treated according to known procedures. If serum containing polyclonal antibodies to an HCV epitope contains antibodies to other antigens, the polyclonal antibodies can be purified by immunoaffinity chromatography. Techniques for producing and processing polyclonal antisera are known in the art, see for example, Mayer and Walker, eds. (1987) IMMUNOCHEMICAL METHODS IN CELL AND MOLECULAR BIOLOGY (Academic Press, London).

One skilled in the art can also readily produce monoclonal antibodies directed against HIV epitopes. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980) HYBRIDOMA TECHNIQUES; Hammerling et al. (1981), MONOCLONAL ANTIBODIES AND T-CELL HYBRIDOMAS; Kennett et al. (1980) MONOCLONAL ANTIBODIES; see also, U.S. Pat. Nos. 4,341,761; 4,399,121; 4,427,783; 4,444,887; 4,466,917; 4,472,500; 4,491,632; and 4,493,890. Panels of monoclonal antibodies produced against HCV epitopes can be screened for various properties; i.e., for isotype, epitope affinity, etc. As used herein, a "single domain antibody" (dAb) is an antibody that is comprised of an HL domain, which binds specifically with a designated antigen. An Ab does not contain a VL domain, but may contain other antigen binding domains known to exist to antibodies, for example, the kappa and lambda domains. Methods for preparing dabs are known in the art. See, for example, Ward et al, Nature 341:544 (1989).

Antibodies can also be comprised of VH and VL domains, as well as other known antigen binding domains. Examples of these types of antibodies and methods for their preparation and known in the art (see, e.g., U.S. Pat. No. 4,816,467), and include the following. For example, "vertebrate antibodies" refers to antibodies that are tetramers or aggregates thereof, comprising light and heavy chains which are usually aggregated in a "Y" configuration and which may or may not have covalent linkages between the chains. In vertebrate antibodies, the amino acid sequences of the chains are homologous with those sequences found in antibodies produced in vertebrates, whether in situ or in vitro (for example, in hybridomas). Vertebrate antibodies include, for example, purified polyclonal antibodies and monoclonal antibodies, methods for the preparation of which are described infra.

"Hybrid antibodies" are antibodies where chains are separately homologous with reference to mammalian antibody chains and represent novel assemblies of them, so that two different antigens are precipitable by the tetramer or aggregate. In hybrid antibodies, one pair of heavy and light chains are homologous to those found in an antibody raised against a first antigen, while a second pair of chains are homologous to those found in an antibody raised against a second antibody. This results in the property of "divalence", i.e., the ability to bind two antigens simultaneously. Such hybrids can also be formed using chimeric chains, as set forth below.

"Chimeric antibodies" refers to antibodies in which the heavy and/or light chains are fusion proteins. Typically, one portion of the amino acid sequences of the chain is homologous to corresponding sequences in an antibody derived from a particular species or a particular class, while the remaining segment of the chain is homologous to the sequences derived from another species and/or class. Usually, the variable region of both light and heavy chains mimics the variable regions or antibodies derived from one species of vertebrates, while the constant portions are homologous to the sequences in the antibodies derived from another species of vertebrates. However, the definition is not limited to this particular example. Also included is any antibody in which either or both of the heavy or light chains are composed of combinations of sequences mimicking the sequences in antibodies of different sources, whether these sources be from differing classes or different species of origin, and whether or not the fusion point is at the variable/constant boundary. Thus, it is possible to produce antibodies in which neither the constant nor the variable region mimic know antibody sequences. It then becomes possible, for example, to construct antibodies whose variable region has a higher specific affinity for a particular antigen, or whose constant region can elicit enhanced complement fixation, or to make other improvements in properties possessed by a particular constant region.

Another example is "altered antibodies", which refers to antibodies in which the naturally occurring amino acid sequence in a vertebrate antibody has been varies. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region can be made to alter antigen-binding characteristics. The antibody can also be engineered to aid the specific delivery of a molecule or substance to a specific cell or tissue site. The desired alterations can be made by known techniques in molecular biology, e.g., recombinant techniques, site-directed mutagenesis, etc.

Yet another example are "univalent antibodies", which are aggregates comprised of a heavy-chain/light-chain dimer bound to the Fc (i.e., stem) region of a second heavy chain. This type of antibody escapes antigenic modulation. See, e.g., Glennie et al. Nature 295:712 (1982). Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab)2), which are capable of selectively reacting with a designated antigen or antigen family. Fab antibodies can be divided into subsets analogous to those described above, i.e., "vertebrate Fab", "hybrid Fab", "chimeric Fab", and "altered Fab". Methods of producing Fab fragments of antibodies are known within the art and include, for example, proteolysis, and synthesis by recombinant techniques.

"Antigen-antibody complex" refers to the complex formed by an antibody that is specifically bound to an epitope on an antigen.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Computer programs are available to determine the likelihood of certain polypeptides to form structures such as β-sheets. One such program, described herein, is the "ALB" program for protein and polypeptide secondary structure calculation and predication. In addition, secondary protein structure can be predicted from the primary amino acid sequence, for example using protein crystal structure and aligning the protein sequence related to the crystal structure (e.g., using Molecular Operating Environment (MOE) programs available from the Chemical Computing Group Inc., Montreal, P.Q., Canada). Other methods of predicting secondary structures are described, for example, in Garnier et al. (1996) Methods Enzymol. 266:540-553; Geourjon et al. (1995)Comput. Applic. Biosci. 11:681-684; Levin (1997) Protein Eng. 10:771-776; and Rost et al. (1993) J. Molec. Biol. 232:584-599.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, a "biological sample" refers to a sample of tissue or fluid isolated from an individual, including but not limited to, for example, blood, plasma, serum, fecal matter, urine, bone marrow, bile, spinal fluid, lymph fluid, samples of the skin, external secretions of the skin, respiratory, intestinal, and genitourinary tracts, samples derived from the gastric epithelium and gastric mucosa, tears, saliva, milk, blood cells, organs, biopsies and also samples of in vitro cell culture constituents including but not limited to conditioned media resulting from the growth of cells and tissues in culture medium, e.g., recombinant cells, and cell components.

The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to fluorescein, rhodamine, danisyl, umbelliferone, Texas red, luminol, acradimum esters, NADPH, beta-galactosidase, horseradish peroxidase, glucose oxidase, alkaline phosphatase and urease.

Overview

The present invention is directed to CD4 mimetics, complexes of Env and CD4 mimetics (Env-CD4 complexes), antibodies to these complexes and the use of compositions comprising a CD4 mimetic and an Env. Without being bound by a particular theory, it appears that it has been difficult to generate immunological responses against Env because the CD4 binding site (and/or the CCR binding site) is buried between the outer domain, the inner domain, and the V1/V2 domains of Env. Thus, although deletion of the V1/V2 domain may render the virus more susceptible to neutralization by monoclonal antibody directed to the CD4 site, the conformation of Env prior to CD4 binding may prevent an antibody response. Thus, the present invention provides CD4 mimetics, and in particular, small molecule CD4 mimetics, that bind to Env and appear to cause a conformational change in Env that exposes one or more epitopes (e.g., "cryptic" or "inducible" epitopes) in or near the CD4 binding site, which in turn allows the generation of an immune response (e.g., a neutralizing antibody response) to Env.

It is to be understood that various forms of the different embodiments of the invention, described herein, may be combined.

CD4 Mimetics

CD4 mimetics described herein include peptoids, small molecules, and peptoid small molecule conjugates that bind to Env polypeptides to induce a conformational change in the Env protein similar or identical to the change induced when Env binds to CD4. The amino acid sequence of CD4 is known and structural studies on CD4 have shown that this molecule is composed of four extracellular immunoglobulin like domains (three containing disulfide linked loops). It is also known that the binding of gp120 to its receptor (CD4) induces conformational changes in the Env protein. However only domain 1 (D1) of CD4 is critical for its interaction with gp120 (Arthos et al. (1989) *Cell* 57(3):469-81; Truneh et al.(1991) *J. Biol Chem* 266(9):5942-8). Mutational analyses, antibody competition experiments combined with the knowledge of three-dimensional structure of CD4 have shown that a region homologous to complementarity determining region 2 (CDR2) of immunoglobulin in D1 plays a major role in gp120 binding (Ryu et al. (1994) *Structure* 2(1):59-74, Sullivan et al. (1998) *J Virol* 72(8):6332-6338).

Indeed, structure resolution of gp120:CD4 complex confirmed that the CDR2-like loop of CD4 is central in CD4-gp120 interaction (Choe & Sodroski (1992) *J Acquir Immune Defic Syndr* 5(2):204-10, Gizachew et al. (1998) *Biochemistry* 37(30):10616-25). In the complex CD4 Phe-43 side chain plugs the entrance of a deep cavity in gp120 and CD4 Arg59, just behind Phe43, is involved in a double H-bond with Asp-368 in gp120.

Crystallographic structure analysis of gp120, in complex with CD4 and the Fab portion the neutralizing monoclonal antibody 17b (Thali et al. (1993) *J. Virol* 67(7):3978-88; Kwong et al. (1998) *Nature* 393:648-659), indicates that a large surface (742 Å2) of the domain D1 of CD4 binds to a large depression (800 Å2) on gp120. The CD4 interface is comprised of 22 residues, contributing to gp120 binding with mixed hydrophobic, electrostatic, H-bonding interactions. The large size and complexity of this interface makes the reproduction of such functional epitope into a small molecule a challenge, and explains the difficulty in the development of small molecule inhibitors of gp120-CD4 interaction. Vita et al. (1998) *Biopolymers* 47:93-100. However, in spite of the large number of residues present in gp120-CD4 interaction surface, studies on hormone-receptor systems showed that only a few residues might dominate the binding energy at the protein-protein interface. Clackson and Wells (1995) *Science* 267(5196):383-386.

Upon binding of gp120 to CD4, unique neutralizing epitopes also appear to be exposed, for example the epitope recognized by the monoclonal antibody CG10 (Gershoni et al. (1993) *Faseb J* 7(12):1185-7). Indeed, while monomeric gp120 protein from lab strains is poorly immunogenic with regard to eliciting primary isolate neutralizing antibodies (Mascola et al. (1996) *J. Infect. Dis.* 173:340-348), monoclonal antibodies that appear to recognize certain epitopes that are exposed on the Env surface once it binds to its CD4 receptor have been shown to neutralize diverse primary isolates. See, e.g., the monoclonal antibody designated 17b (Thali et al. (1993) J Virol 67(7):3978-3988). However, cross-clade primary isolate neutralizing antibody responses using receptor/co-receptor complexed Env have been attributed to the immunogenicity of the gp41 fusion domain. Lacasse et al (1999) *Science* 283:357-362.

Additionally, attempts to evaluate gp120-CD4 complexes as potential vaccine candidate for inducing high avidity and primary isolate neutralizing antibodies have been thwarted by the concern that an immune response could be generated against CD4 itself thereby raising autoimmune and safety issues. (D'Souza et al. (1997) *J. Infect Dis.* 175:1056-62, DeVico et al. (1995) *Virology* 211(2):583-588).

Thus, the present invention pertains, in part, to CD4 mimetics that bind to HIV Env polypeptides and when bound, induce a conformational change in Env similar to that induced by binding to CD4.

In other embodiments the immunological compositions provided by the present invention include small molecule compounds that are known to be competitive CD4 inhibitors of a gp120 polypeptide (Shaoxing, C. et. al. Design and synthesis of a CD4, β-turn mimetic that inhibits human immunodeficiency virus envelope glycoprotein gp120 binding and infection of human lymphocytes, *Proc. Natl. Acad. Sci.*, (1992), 89, 5872-5876; WO 99/24065, WO 03/072028, U.S. Pat. Nos. 6,469,006 and 6,476,034).

In still other embodiments, the present invention provides immunological compositions containing novel small molecule CD4 mimetics. These small molecules are commercially available or may be synthesized by one of skill in the art by adapting the procedures set forth in WO 03/072028, U.S. Pat. No. 6,469,006, and U.S. Pat. No. 6,476,034.

In particular, preferred CD4 mimetics are small molecules having a molecular weight of less than about 2500 daltons. However, more typically, a small molecule CD4-mimetic in accordance with the invention will possess a molecular weight falling within one of the following ranges: less than about 1500, less than about 1000, less than about 900, less than about 800, less than about 700, less than about 600 or less than about 500.

Certain small molecule CD4 mimetics of the invention were identified by first screening molecules having a degree of structural similarity to CD4M33, a known CD4 mimetic (Martin et al (2003), Nat Biotechnol. 21(7):71-76), as described in detail in Example 1. In examining small molecules having the desired features (e.g., the ability, when complexed to an Env protein, to inhibit CD4 binding thereto, and/or upregulate CD4 inducible epitopes on the resulting Env protein-CD4 mimetic complex), the Applicant discovered that the small molecules shared certain structural similarities with one another.

That is to say, preferred small molecule CD4 mimetics of the invention typically although do not necessarily comprise a fused bicyclic or tricyclic core structure. Illustrative core structures include aromatic ring systems, optionally containing one or more heteroatoms, such as an indole, a pyrrolopyridine, and a fluorenone. Preferably, a small molecule CD4 mimetic in accordance with the invention comprises one of the following core structures:

V

VI where in structure V, none or one of ring carbons 4, 5, 6, or 7 may be replaced by a nitrogen. Structure V represents an indole core structure, while replacement of any one of ring carbons 4, 5, 6, or 7 results in a pyrrolopyridine. Pyrrolopyridine core structures include:

V-a

1H-Pyrrolo[2,3-c]pyridine

V-b

1H-Pyrrolo[2,3-b]pyridine

V-c

1H-Pyrrolo[3,2-b]pyridine

V-d

1H-Pyrrolo[3,2-c]pyridine

Structure VI is a fluoren-9-one.

In certain instances, in each of core structures V and VI, one of the ring atoms is covalently attached, via an optional linker, J, to a substituted or unsubstituted piperidine or piperazine, which itself may form part of a bicyclic ring structure, such as a tetrahydro-isoquinolone, whose parent structure is shown below.

VII 1,2,3,4-Tetrahydro-isoquinoline

An illustrative bicyclic ring structure formed by a piperidine includes the following illustrative substituted tetrahydro-isoquinolone, although any of a number of different substituents may be present on the tetrahydro-isoquinolone ring.

VIII

3-Oxomethylene-2-(1,2,3,4-tetrahydro-isoquinolin-1-ylmethyl)-2,3-dihydro-isoindol-1-one Any of a number of optional substituents may be present on the core structures, that is to say, covalently attached to one or more ring atom positions. For example, suitable substituents include $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, halogen, —CN, phenyl, benzyl, nitro, $C_1$-$C_6$ alkoxy, $C_3$-$C_6$ cycloalkoxy, benzyloxy, —C(O)—$C_1$-$C_6$ alkyl, —C(O)—$C_6H_5$—, and, for example, —C(O)—$C_6H_4$—W, wherein W is an ortho, meta, or para-halogen As stated previously, the small molecule CD4 mimetic may optionally comprise a linker, J. Typically, the linker J ranges from about 1 to about 50 atoms in length. More preferably, J ranges from about 1 to about 40 atoms in length, or from about 1 to about 30 atoms in length. Representative linkers shown explicitly herein generally have a length of 1, 2, 3, 4, 5, 6, 7, 8, 9, 10, 11, 12, 13, 14, 15, 16, 17, 19, 19 or 20 atoms.

Linkers of the invention include the following: —O—, —S—, —S—S—, —C(O)—, —O—C(O)—, —C(O)—O—, —C(O)—C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—, —CH$_2$—, —CH$_2$—CH$_2$—O—CH$_2$, —CH$_2$—CH$_2$—CH$_2$—O—, —O—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —CH(OH) CH$_2$—C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—, —NH—C(O)—CH$_2$—, —NH—C(O)-furanyl, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —NH—CH$_2$—, —C(O)—CH$_2$—, —C(O)—CH(CH$_3$)—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—

$CH_2$—, —$CH_2$—$CH_2$—C(O)—, —$CH_2$—$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, —$CH_2$—$CH_2$—$CH_2$—C(O)—NH—$CH_2$—$CH_2$—NH—C(O)—$CH_2$—$CH_2$—, —O—C(O)—NH—$[CH_2]_{0-6}$—$(OCH_2CH_2)_{0-2}$—, —C(O)—NH—$(CH_2)_{1-6}$—NH—C(O)—, —NH—C(O)—NH—$(CH_2)_{1-6}$—NH—C(O)—, —O—C(O)—$CH_2$—, —O—C(O)—$CH_2$—$CH_2$—, and —O—C(O)—$CH_2$—$CH_2$—$CH_2$—. Preferred linkers include, in one embodiment, —C(O)$CH_2$—C(O)—, —C(O)—$CHCH_3$—, —C(O)—C(O)—, —CH(OH)$CH_2$—, —$CH_2$—, —N=C(O)-furanyl, in either orientation.

In yet another embodiment, a small molecule CD4 mimetic in accordance with the invention is characterized by one of the following structures:

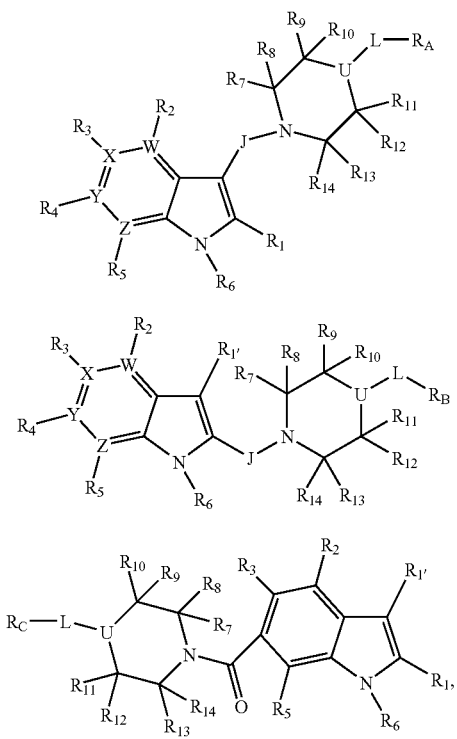

where in each of structures I, II and III:

W, X, Y, and Z are each independently selected from the group consisting of carbon and nitrogen, provided that no more than one of W, X, Y, or Z is nitrogen;

$R_1$, $R_{1'}$, $R_2$, $R_3$, $R_4$, $R_5$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, halogen, CN, phenyl, nitro, OC(O)$R_{15}$, C(O)$R_{15}$, C(O)O$R_{16}$, C(O)NR$_{17}$R$_{18}$, OR$_{19}$, SR$_{20}$, and NR$_{21}$R$_{22}$, each of said alkyl and cycloalkyl being optionally substituted with one to three substituents independently selected from halogen, CN, $NO_2$, OC(O)$R_{15}$, C(O)$R_{15}$, C(O)O$R_{15}$, C(O)NR$_{17}$R$_{18}$, OR$_{19}$, SR$_{20}$, and NR$_{21}$R$_{22}$, with the proviso that $R_2$, $R_3$, $R_4$, or $R_5$ is absent when the ring atom to which it is attached is a double-bonded nitrogen, i.e., a trivalent nitrogen;

$R_{15}$ is independently selected from the group consisting of H, $C_1$-$C_6$ alkyl, $C_3$-$C_6$ cycloalkyl, $C_2$-$C_6$ alkenyl, and $C_4$-$C_6$ cycloalkenyl;

$R_{16}$, $R_{19}$, and $R_{20}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_3$-$C_6$ alkynyl, phenyl, and benzyl, wherein each of said alkyl, cycloalkyl, phenyl, and benzyl are optionally substituted with one, two, or three substituents selected from the group consisting of halogen, NR$_{21}$R$_{22}$, OH, CN, or $NO_2$; provided the carbon atoms that comprise the carbon-carbon triple bond of said $C_3$-$C_6$ alkynyl are not the point of attachment to the oxygen or sulfur to which $R_{16}$, $R_{19}$, or $R_{20}$ is attached;

$R_{17}$ and $R_{18}$ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl, wherein each of said alkyl and cycloalkyl are optionally substituted with one, two, or three substituents selected from the group consisting of halogen, NR$_{21}$R$_{22}$, OH, CN, or $NO_2$; provided the carbon atoms that comprise the carbon-carbon double bond of said $C_3$-$C_6$ alkenyl or the carbon-carbon triple bond of said $C_3$-$C_6$ alkynyl are not the point of attachment to the nitrogen to which $R_{17}$ and $R_{18}$ is attached;

$R_{21}$, and $R_{22}$ are each independently selected from the group consisting of H, OH, $C_1$-$C_6$ alkyl, $C_3$-$C_6$ cycloalkyl, $C_3$-$C_6$ alkenyl, $C_5$-$C_6$ cycloalkenyl, $C_3$-$C_6$ alkynyl, phenyl, and C(O)$R_{23}$; provided the carbon atoms that comprise the carbon-carbon double bond of said $C_3$-$C_6$ alkenyl, $C_4$-$C_6$ cycloalkenyl, or the carbon-carbon triple bond of said $C_3$-$C_6$ alkynyl are not the point of attachment to the nitrogen to which $R_{21}$ and $R_{22}$ is attached;

$R_{23}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_2$-$C_6$ alkynyl;

$R_6$ is $(CH_2)_n$Q, wherein n is 0-6;

Q is selected from:

(1) H, $C_1$-$C_6$ alkyl, $C_3$-$C_6$ cycloalkyl, $C_2$-$C_6$ alkenyl, $C_4$-$C_6$ cycloalkenyl, $C_3$-$C_6$ alkynyl, halogen, CN, Ar, $NO_2$, C(O)$R_{24}$, C(O)O$R_{25}$, C(O)NR$_{26}$R$_{27}$, COOAr, TR$_6$, NR$_{21}$R$_{22}$, NC(O)NR$_{21}$R$_{22}$, OC(O)$R_{16}$, $(N(R_{21})_2)$C=N-T-$R_{22}$, C(O)Ar, or S(O)$_m$R$_{21}$;

(2) a 4-7 membered heterocyclic ring, optionally substituted with $R_{16}$, which may contain 1-3 heteroatoms selected from the group consisting of O, S, SO, $SO_2$, N, and NR$_{24}$;

T is S or O;

m is 0-2;

$R_{24}$ is selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl;

$R_{25}$ is selected from the group consisting of $C_1$-$C_6$ alkyl, $C_3$-$C_6$ cycloalkyl, $C_2$-$C_6$ alkenyl, $C_4$-$C_6$ cycloalkenyl, and $C_3$-$C_6$ alkynyl; provided the carbon atoms that comprise the carbon-carbon triple bond of said $C_3$-$C_6$ alkynyl are not the point of attachment to the oxygen to which $R_{25}$ is attached;

$R_{26}$ and $R_{27}$ are each independently selected from the group consisting of H, $C_1$-$C_6$ alkyl, $C_3$-$C_6$ cycloalkyl, $C_3$-$C_6$ alkenyl, $C_5$-$C_6$ cycloalkenyl, and $C_3$-$C_6$ alkynyl; provide carbon atoms that comprise the carbon-carbon double bond of said $C_3$-$C_6$ alkenyl, $C_5$-$C_6$ cycloalkenyl, or the carbon-carbon triple bond of said $C_3$-$C_6$ alkynyl are not the point of attachment to the nitrogen to which $R_{26}$ and $R_{27}$ are attached;

$R_7$, $R_8$, $R_9$, $R_{10}$, $R_{11}$, $R_{12}$, $R_{13}$, and $R_{14}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, CR$_{28}$R$_{29}$OR$_{30}$, C(O)$R_{31}$, CR$_{32}$(OR$_{33}$)OR$_{34}$, CR$_{35}$NR$_{36}$R$_{37}$, C(O)OR$_{38}$, C(O)NR$_{39}$R$_{40}$, CR$_{41}$R$_{42}$F, CR$_{43}$F$_2$, and CF$_3$, each of said alkyl and cycloalkyl being optionally substituted with one to three substituents independently selected from halogen, CN, $NO_2$, OC(O)$R_{15}$, C(O)$R_{15}$, C(O)

OR₁₅, C(O)NR₁₇R₁₈, OR₁₉, SR₂₀, and NR₂₁R₂₂, or R₈ and R₉ may be absent such that the carbon ring atoms to which each is independently attached together form a double bond.

R₂₈, R₂₉, R₃₀, R₃₁, R₃₂, R₃₅, R₄₁, R₄₂ and R₄₃ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, and C(O)R₄₄;

R₃₃, R₃₄ and R₃₈ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl; provided the carbon atoms that comprise the carbon-carbon triple bond of said $C_3$-$C_6$ alkynyl are not the point of attachment to the oxygen to which R₃₄ and R₃₈ are attached;

R₃₆ and R₃₇ are each independently selected from the group consisting of H, $C_1$-$C_6$ alkyl, $C_1$-$C_6$ cycloalkyl, $C_3$-$C_6$ alkenyl, $C_4$-$C_6$ cycloalkenyl, and $C_3$-$C_6$ alkynyl; provided the carbon atoms that comprise the carbon-carbon triple bond of said $C_3$-$C_6$ alkynyl are not the point of attachment to the nitrogen to which R₃₆ and R₃₇ are attached;

R₃₉ and R₄₀ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_3$-$C_6$ alkynyl; provided the carbon atoms that comprise the carbon-carbon triple bond of said $C_3$-$C_6$ alkynyl are not the point of attachment to the nitrogen to which R₃₉ and R₄₀ are attached; R₄₄ is selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_2$-$C_6$ alkynyl;

J is —(CO)—, —(CO)CH₂—, —(CO)(CO)—, or —(CO)CHR₉—;

U is nitrogen or CH;

L is —(CO)— or —CH₂—;

$R_A$, $R_B$, and $R_C$ are independently selected from the group consisting of Ar, H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, halogen, CN, nitro, OC(O)R₁₅, C(O)R₁₅, C(O)OR₁₆, C(O)NR₁₇R₁₈, OR₁₉, SR₂₀ and NR₂₁R₂₂, each of said alkyl and cycloalkyl being optionally substituted with one to three substituents independently selected from halogen, CN, NO₂, OC(O)R₁₅, C(O)R₁₅, C(O)OR₁₅, C(O)NR₁₇R₁₈, OR₁₉, SR₂₀, and NR₂₁R₂₂;

Ar is a 5-12 membered aromatic ring optionally containing one to five heteroatoms independently selected from the group consisting of O, S, N, or NR₁₆ and optionally substituted with one to six substituents independently selected from the group consisting of R₄₅, R₄₆, R₄₇, R₄₈, or R₄₉;

R₄₅, R₄₆, R₄₇, R₄₈, and R₄₉ are each independently H, $C_1$-$C_6$ alkyl, $C_3$-$C_6$ cycloalkyl, $C_2$-$C_6$ alkenyl, $C_3$-$C_6$ cycloalkenyl, $C_2$-$C_6$ alkynyl, halogen, CN, nitro, C(O)R₄₅, COOR₄₆, hydroxyl, hydroxymethyl, trifluoromethyl, trifluoromethoxy, O-benzyl, O-phenyl, OC(O)$C_1$-$C_6$ allcyl, SC(O)$C_1$-$C_6$ alkyl, S(O)$_m$$C_1$-$C_6$ alkyl, S(O)₂ NR₂₁R₂₂, O—V, CH₂(CH₂)$_p$—V, O(CH₂)——V, (CH₂)$_p$O—V, CH=CH—V, or TR₄₇, each of said alkyl and cycloalkyl being optionally substituted with one to three substituents independently selected from the group consisting of, NR₂₁NR₂₂, OH, CN, or NO₂;

V is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl;

p is 1-2;

R₄₅ and R₄₆ are each independently H, $C_1$-$C_6$ alkyl, or $C_3$-$C_6$ cycloalkyl;

R₄₇ is H, $C_1$-$C_6$ alkyl, $C_3$-$C_6$ cycloalkyl, $C_2$-$C_6$ alkenyl, $C_3$-$C_6$ cycloalkenyl, $C_2$-$C_6$ alkynyl, C(O)R₄₈ or C(O)OR₄₉, each of said alkyl and cycloalkyl being optionally substituted with one to three substituents independently selected from the group consisting of, NR₂₁NR₂₂, OH, CN, or NO₂; and R₄₈, R₄₉ are each independently H, $C_1$-$C_6$ alkyl, or $C_3$-$C_6$ cycloalkyl, each of said alkyl and cycloalkyl being optionally substituted with one to three substituents independently selected from the group consisting of, NR₂₁NR₂₂, OH, CN, or NO₂.

Small molecule CD4 mimetics in accordance with the invention exclude the following:

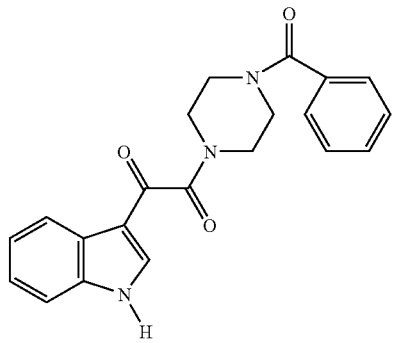

IX

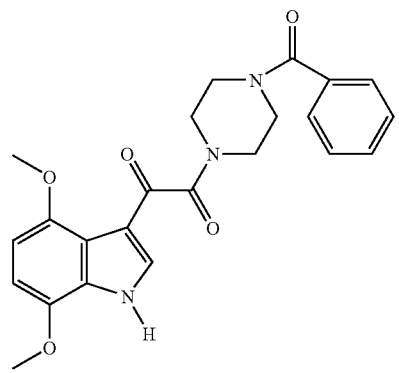

X

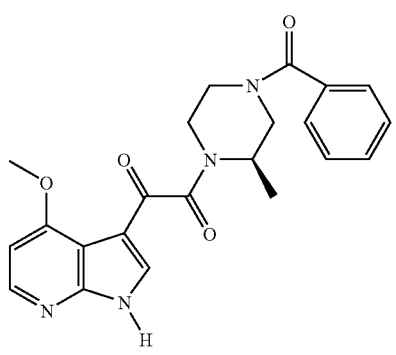

XI

Additional illustrative small molecule CD4 mimetics (compounds 1-30) in accordance with the invention and their corresponding structures are provided in Tables 1-4 herein. For instance, preferred small molecule CD4 mimetics include 1-[4-(1H-Indole-6-carbonyl)-piperazin-1-yl]-2,2-diphenyl-ethanone (11); [4-(1H-Indole-6-carbonyl)-piperazin-1-yl]-(3,4,5-trimethoxy-phenyl)-methanone (8); [4-(1H-Indol-3-yl)-piperidin-1-yl]-(3,4,5-trimethoxy-phenyl)-methanone (12); (5-Benzyloxy-3-methyl-1H-indol-2-yl)-(4-methyl-piperazin-1-yl)-methanone (13); (5-Benzyloxy-3-methyl-1H-indol-2-yl)-morpholin-4-yl-methanone (14); 2-{2-[2-(2-Methyl-1H-indol-3-yl)-2-oxo-ethyl]-1,2,3,4-tetrahydro-isoquinolin-1-ylmethyl}-isoindole-1,3-dione (15); 1-[2-(2-Methyl-propenyl)-1H-indol-3-yl]-2-morpholin-4-yl-ethane-1,2-dione (16); (5-Methoxy-1,2-dimethyl-1H-indol-3-yl)-

(4-methyl-piperazin-1-yl)-methanone (17); and 2-[1-(4-Chloro-benzoyl)-5-methoxy-2-methyl-1H-indol-3-yl]-1-(4-phenyl-piperazin-1-yl)-ethanone (18), 2-(4-Benzyl-piperazin-1-yl)-1-(5-methoxy-1H-indol-3-yl)-ethanone (2); 2-{2-[2-(1H-Indol-3-yl)-2-oxo-ethyl]-1,2,3,4-tetrahydro-isoquinolin-1-ylmethyl}-isoindole-1,3-dione (20); 1-[2-(5-Methoxy-1,2-dimethyl-1H-indol-3-yl)-2-oxo-ethyl]-piperidine-4-carboxylic acid amide (21); 4-[2-Hydroxy-2-(5-methoxy-1H-indol-3-yl)-ethyl]-piperazine-1-carboxylic acid ethyl ester (22); 1-[2-(5-Methoxy-1H-indol-3-yl)-2-oxo-ethyl]-piperidine-4-carboxylic acid ethyl ester (23), 1-(1H-Indol-3-yl)-2-piperidin-1-yl-ethane-1,2-dione (19); [4-(1H-Indol-3-ylmethyl)-piperazin-1-yl]-(3,4,5-trimethoxy-phenyl)-methanone (20); 1-(1H-Indol-3-yl)-2-morpholin-4-yl-ethane-1,2-dione (21); (5-Benzyloxy-3-methyl-1H-indol-2-yl)-piperidin-1-yl-methanone (22); Furan-2-carboxylic acid (1-benzyl-piperidin-4-yl)-(2,3-dimethyl-1H-indol-7-yl)-amide (23); (5-Benzyloxy-3-methyl-1H-indol-2-yl)-(4-phenyl-piperazin-1-yl)-methanone (24);[4-(1H-Indol-3-ylmethyl)-piperazin-1-yl]-(2-methoxy-phenyl)-methanone (25); 2-[4-(2-Methoxy-phenyl)-piperazin-1-yl]-1-(2-methyl-1H-indol-3-yl)-ethanone (26); 2-{2-[2-Hydroxy-2-(5-methoxy-1H-indol-3-yl)-ethyl]-1,2,3,4-tetrahydro-isoquinolin-1-ylmethyl}-isoindole-1,3-dione (27); 2-[4-(2-Hydroxy-ethyl)-piperazin-1-yl]-1-(5-methoxy-1H-indol-3-yl)-ethanone (28); 2-{2-[2-(5-Methoxy-1H-indol-3-yl)-2-oxo-ethyl]-1,2,3,4-tetrahydro-isoquinolin-1-ylmethyl}-isoindole-1,3-dione (29); {4-[2-(5-Methoxy-1H-indol-3-yl)-2-oxo-ethyl]-piperazin-1-yl}-acetic acid methyl ester (30); 1-[2-(5-methoxy-1H-indol-3-yl)-2-oxoethyl]piperidine-4-carboxamide (1); 2-(4-benzylpiperazin-1-yl)-1-(5-methoxy-1H-indol-3-yl)ethanone (2); {1-[(4,6-dimethyl-1H-indol-2-yl)carbonyl]piperidin-4-yl}(4-fluorophenyl)methanone (3); 1-[2-(5-methoxy-1,2-dimethyl-1H-indol-3-yl)-1-methyl-2-oxoethyl]piperidine-4-carboxamide (4); ethyl 1-[(4,6-dimethyl-1H-indol-2-yl)carbonyl]piperidine-4-carboxylate (5); 6-{[4-(2,6-difluorobenzoyl)piperazin-1-yl]carbonyl}-1H-indole (6); 2-{[4-(1H-indol-6-ylcarbonyl)piperazin-1-yl]carbonyl}phenyl acetate (7); 6-{[4-(3,4,5-trimethoxybenzoyl)piperazin-1-yl]carbonyl}-1H-indole (8); 1-[2-(5-methoxy-1,2-dimethyl-1H-indol-3-yl)-2-oxoethyl]piperidine-4-carboxamide (9); and 4-{[4-(2-furoyl)piperazin-1-yl]carbonyl}-9H-fluoren-9-one (10).

Peptoids

Peptoids are an easily synthesized class of peptidomimetic oligomer that are highly diverse in structure and are stable to enzymatic and chemical degradation (Miller, S. M. et al. Proteolytic Studies of Homologous peptide and N-Substituted Glycine Peptoid Oligomers. *Bioorg. Med. Chem. Lett.* (1994), 4, 2657-2662).

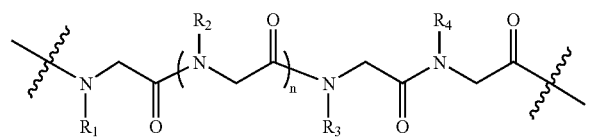

Hundreds of different side chains can be incorporated into the polymer, including polar, reactive and even heterocyclic functionalities [Zuckermann, R. N., Kerr, J. M., Kent, S. B. H. & Moos, W. H. Efficient Method for the Preparation of Peptoids [Oligo(N-substituted glycines)] by Submonomer Solid Phase Synthesis. *J. Am. Chem. Soc.* (1992), 114, 10646-10647; Figliozzi, G. M., Goldsmith, R., Ng, S., Banville, S. C. & Zuckermann, R. N. Synthesis of N-(substituted)glycine Peptoid Libraries. *Methods Enzymol.* (1996), 267, 437-447; Burkoth, T. S., Fafarman, A. T., Charych, D. H., Connolly, M. D. & Zuckermann, R. N. Incorporation of Unprotected Heterocyclic Side Chains into Peptoid Oligomers via Solid-Phase Submonomer Synthesis. *J. Am. Chem. Soc.* (2003), 125, 8841-8845; Uno, T., Beausoleil, E., Goldsmith, R. A., Levine, B. H. & Zuckermann, R. N. New Submonomers for Poly N-Substituted Glycines (Peptoids). *Tetrahedron Lett.* (1999), 40, 1475-1478]. The ability to efficiently incorporate a wide variety of structural features allows rapid synthesis of biomimetic oligomers with far more chemical diversity than natural peptides.

The present invention provides peptoid CD4 mimetics. Thus in some embodiments, the present invention provides peptoid mimics of key CD4 binding residues such as Phe43 and Arg59. In other embodiments, the peptoids further mimic the CD4 beta-turn motif by incorporating a beta-turn inducing amino acid such as Fmoc-3-amino-1-carboxymethylcaprolactam.

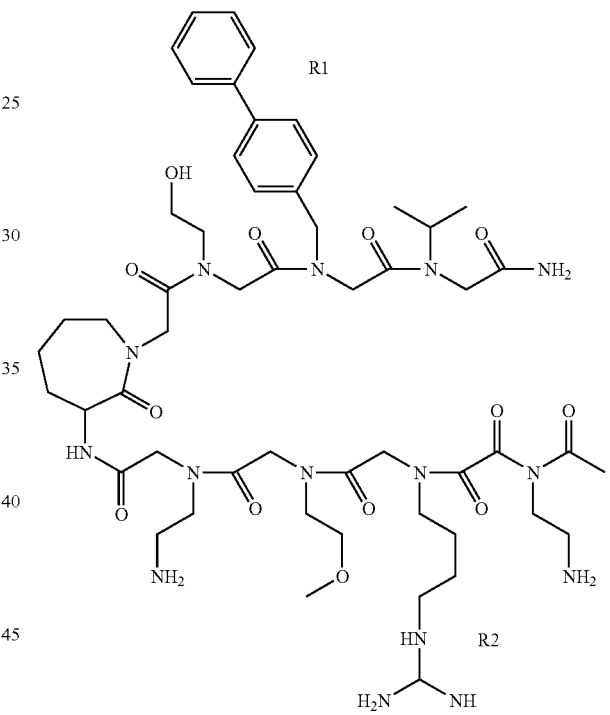

In one embodiment, the invention provides peptoids having at least twelve monomer units. In other embodiments, the invention provides peptoids having at least ten, nine, eight, seven, six, five, four, or three monomer units.

In some embodiments, the peptoids provided by the present invention are linked to small molecules to form a peptoid small molecule conjugate. In some particular embodiments, the small molecules are modified with a peptoid trimer. Methods to conjugate small molecules to combinatorial libraries of peptoid oligomers are known (Horn, T., Lee, B.-C., Dill, K. A. & Zuckermann, R. N. Incorporation of Chemoselective Functionalities into Peptoids via Solid-Phase Submonomer Synthesis. *Bioconj. Chem.* 15, 428-435 (2004). The method involves the solid-phase synthesis of an oligomer library, where each compound is functionalized with a chemoselective ligation group, facilitating the attachment of the small molecule to a specific position of the oligomer. Alternatively, amino groups are introduced into tolerant positions of the small molecule and the amino-small molecule is used as a peptoid submonomer to be incorporated at any position of the oligomer. These positions are then modified with either amino or carboxyl groups to facilitate their attachment to, or incorporation in a combinatorial oligomer library.

Crosslinked Peptoids, Small Molecules, and Peptoid Small Molecule Conjugates

In some embodiments, the invention provides peptoids, small molecules, and peptoid small molecule conjugates that are crosslinked to an Env polypeptide. In some particular embodiments, the invention provides peptoids, small molecules, and peptoid small molecule conjugates having a spacer and crosslinking moiety.

The spacer or linker varies in length and, in some embodiments, is constructed from a combination of various aminoalkyl acids and di-acids to span distances from 5-50 angstroms. Suitable spacers typically have an atom length of from about 3 to about 50 atoms. A cross linking moiety comprising a terminal reactive group (e.g. benzophenone) is placed at the end of the linker. After contacting the Env polypeptide with the peptoid, small molecule, or peptoid small molecule conjugate, both the Env polypeptide and the compound are then reacted to form a covalently bound Env polypeptide/compound complex.

Env Polypeptides

The Env polypeptide portion of the complexes described herein can be derived from an envelope protein, preferably from HIV Env. As noted above, the envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp 120 is released from the surface of virions and infected cells. Env polypeptides may also include gp140 polypeptides.

In certain embodiments, the Env polypeptide component of the complex is a monomer or a dimer. In preferred embodiments, the Env polypeptide component is an oligomeric Env polypeptide (e.g., a trimer). The primary sequence of the Env polypeptide precursor of HIV-1$_{SF2}$ (hereinafter "SMF2") strain is known. See, e.g., FIG. 1 of International Publication WO 04/037847. Env polypeptides contain multiple N-linked glycosylation sites, for example the HIV strain SMF2 contains approximately 24 N-linked glycosylation sites. As suggested by their name, the hypervariable domains contain extensive amino acid substitutions, insertions and deletions as between strains. Despite this variation, most, if not all, Env polypeptide sequences preserve the virus's ability to bind to the viral receptor CD4. Further, alignment of the amino acid sequences of Env polypeptide of any HIV variant can be determined relative to other variants, such as HXB-2, as described for example, in WO 00/39303. In other embodiments, the Env polypeptide comprises an oligomeric form of Env, for example oligomeric gp140 (o-gp140).

The Env polypeptide component of the Env-CD4 complex can be derived any known mHV isolates, as well as newly identified isolates, and subtypes of these isolates. Descriptions of structural features can be given herein with reference to SMF 2or HXB-2. One of ordinary skill in the art in view of the teachings of the present disclosure and the art can determine corresponding regions in other HIV variants (e.g., isolates HIV$_{IIIb}$, HIV-1$_{SF162}$, HIV-1$_{SF170}$, HIV$_{LAV}$, HIV$_{LAI}$, HIV$_{MN}$, HIV-1$_{CM235}$, HIV-1$_{US4}$, other HIV-1 strains from diverse subtypes (e.g., subtypes, A through G, and O), HIV-2; strains and diverse subtypes (e.g., HIV-2$_{UC1}$ and HIV-2$_{UC2}$), and simian immunodeficiency virus (SIV). (See, e.g., Virology, 3rd Edition (W. K. Joklik ed. 1988); Fundamental Virology, 2nd Edition (B. N. Fields and D. M. Knipe, eds. 1991); Virology, 3rd Edition (Fields, B. N., D. M. Knipe, P. M. Howley, Editors, 1996, Lippincoff-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify □-sheet regions). The actual amino acid sequences of the modified Env polypeptides can be based on any HIV variant.

The Env polypeptides described herein may include additional modifications to the native sequence, such as additional internal deletions, additions and substitutions. These modifications may be deliberate, as through site-directed mutagenesis, or may be accidental, such as through naturally occurring mutational events. Thus, for example, if the Env polypeptide is to be used in vaccine compositions, the modifications must be such that immunological activity (i.e., the ability to elicit an antibody response to the polypeptide) is not lost. Similarly, if the polypeptides are to be used for diagnostic purposes, such capability must be retained. The Env polypeptides described herein can be monomeric or oligomeric.

The Env polypeptides of the present invention can be produced in any number of ways all of which are well known in the art, including, for example, peptide synthesis techniques, recombinant production and the like. See, e.g., Srivastava et al. (2003) J. Virol. 77(20):11244-11259 describing production of oligomeric Env proteins.

Env-CD4 Complexes

The present invention also encompasses complexes of CD4 mimetics and Env polypeptides that are effective to change the conformation of the Env polypeptide and expose epitopes that elicit production of antibodies, particularly neutralizing antibodies. The Env-CD4 mimetic complexes may be formed in vivo or, alternatively, complexes may be formed in vitro or ex vivo, for example in order to generate antibody production. The antibodies may then be used in pharmaceutical compositions for administration to a subject.

Env and CD4 mimetics as described herein can be complexed in a variety of ways. In certain embodiments, Env and CD4 proteins are complexed in a reaction mixture, for example using one or more cross-linking agents, such as formaldehyde, glutyraldehyde and the like. In other embodiments, a CD4 mimetic is linked to the envelope by a specific covalent bond which will not perturb the envelope exposed antigenic surface, yet exposing the cryptic conserved epitopes that are normally not accessible, for example so that an antibody response can be mounted. In still further embodiments, a fixative such as formalin is used to complex Env and CD4 proteins. CD4 mimetics are complexed or linked with Env to maintain the exposure of CD4-inducible epitopes in the Env protein for immunization purposes to target the functional epitopes for vaccine applications.

A pH near physiological pH is most preferred since it is believed to more accurately mimic binding of CD4 to Env in vivo. The most favorable pH for promoting complexing can be determined by one skilled in the art, and will depend upon the particular protein to be modified. Suitable buffers include sodium phosphate, sodium acetate, sodium carbonate, and phosphate buffered saline (PBS). Typically, the CD4 mimetic is added to the protein-containing solution at an equimolar amount or at a molar excess relative to target protein, for instance molar ratio of about 1:1, 1.5:1, 2:1, 3:1, 4:1, 5:1, 6:1, 8:1, or 10:1.

The complexing reactions are typically carried out at temperatures at or near about physiological temperatures 37° C.), although temperatures may range from about −15° C. to about 45° C., more preferably from about 25° C. to 40° C., for approximately one to twenty four hours. The exact reaction time may vary. Binding of CD4 mimetics to Env can be determined using a variety of techniques, for example, HPLC, ELISA and Biacore's surface plasmon resonance (SPR) systems (Biacore Inc, Piscataway, N.J.). See, also, FIGS. 1 and 2.

In addition, suitable CD4 mimetic-Env complexes may be produced in vivo, by administering one or more CD4 mimetics as described herein to a subject under conditions such that the CD4 mimetic binds to Env polypeptides in the subject. Administration of CD4 mimetics to the subject can be readily accomplished and is described below.

Antibodies

Antibodies, both monoclonal and polyclonal, which are directed against epitopes on Env-CD4 mimetic complexes (and cryptic epitopes exposed by binding of CD4 mimetics to Env) are particularly useful in diagnosis and therapeutic applications, for example, those antibodies which are neutralizing are useful in passive immunotherapy. Monoclonal antibodies, in particular, may be used to raise anti-idiotype antibodies.

Anti-idiotype antibodies are immunoglobulins that carry an "internal image" of the antigen of the infectious agent against which protection is desired. Techniques for raising anti-idiotype antibodies are known in the art. See, e.g., Grzych (1985), Nature 316:74; MacNamara et al. (1984), Science 226:1325, Uytdehaag et al (1985), J. Immunol. 134: 1225. These anti-idiotype antibodies may also be useful for treatment and/or diagnosis of HIV.

An immunoassay for viral antigen may use, for example, a monoclonal antibody directed towards a viral epitope, a combination of monoclonal antibodies directed towards epitopes of one viral polypeptide, monoclonal antibodies directed towards epitopes of different viral polypeptides, polyclonal antibodies directed towards the same viral antigen, polyclonal antibodies directed towards different viral antigens or a combination of monoclonal and polyclonal antibodies.

Immunoassay protocols may be based, for example, upon competition, or direct reaction, or sandwich type assays. Protocols may also, for example, use solid supports, or may be by immunoprecipitation. Most assays involve the use of labeled antibody or polypeptide. The labels may be, for example, fluorescent, chemiluminescent, radioactive, or dye molecules. Assays which amplify the signals from the probe are also known. Examples of which are assays which utilize biotin and avidin, and enzyme-labeled and mediated immunoassays, such as ELISA assays.

An enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microplate or plastic cup), incubated with test serum dilutions, washed, incubated with anti-immunoglobulin labeled with an enzyme, and washed again. Enzymes suitable for labeling are known in the art, and include, for example, horseradish peroxidase. Enzyme activity bound to the solid phase is measured by adding the specific substrate, and determining product formation or substrate utilization colorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is estimated colorimetrically, and related to antigen concentration.

Polyclonal antibodies can be produced by administering the fusion protein to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against epitopes exposed by binding of CD4 to Env can also be produced. Normal B cells from a mammal, such as a mouse, immunized with, e.g., an Env-CD4 complex as described herein can be fused with, for example, HAT-sensitive mouse myeloma cells to produce hybridomas. Hybridomas producing antibodies specific for epitopes exposed when CD4 miniproteins bind to Env can be identified using RIA or ELISA and isolated by cloning in semi-solid agar or by limiting dilution. Clones producing the desired specific antibodies are isolated by another round of screening.

Antibodies, monoclonal and/or polyclonal, which are directed against epitopes, are particularly useful for detecting the presence of antigens in a sample, such as a serum sample from an HIV-infected human. An immunoassay for an HIV antigen may utilize one antibody or several antibodies. An immunoassay for an HIV antigen may use, for example, a monoclonal antibody directed towards an HIV epitope, a combination of monoclonal antibodies directed towards epitopes of one Env or Env-CD4 polypeptide, monoclonal antibodies directed towards epitopes of different polypeptides, polyclonal antibodies directed towards the same HIV antigen, polyclonal antibodies directed towards different HIV antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate Env or CD4 complexed-Env by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind the target from a biological sample, such as blood or plasma. The bound proteins or complexes are recovered from the column matrix by, for example, a change in pH.

Diagnostic, Vaccine and Therapeutic Applications

The CD4 mimetics, Env-CD4 mimetic complexes and antibodies thereto can be used for a number of diagnostic and therapeutic purposes. For example, as noted above, the antibodies generated against the same, can be used in a variety of assays, to determine the presence of reactive antibodies/and or Env proteins in a biological sample to aid in the diagnosis of HIV infection or disease status or as measure of response to immunization.

As noted above, the presence of antibodies reactive with the Env (e.g., gp120) polypeptides and, conversely, antigens reactive with antibodies generated thereto, can be detected using standard electrophoretic and immunodiagnostic techniques, including immunoassays such as competition, direct reaction, or sandwich type assays. Such assays include, but are not limited to, western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the antigen and the antibody or antibodies reacted therewith.

Solid supports can be used in the assays such as nitrocellulose, in membrane or microtiter well form; polyvinylchloride, in sheets or microtiter wells; polystyrene latex, in beads or microtiter plates; polyvinylidine fluoride; diazotized paper; nylon membranes; activated beads, and the like.

Typically, the solid support is first reacted with the biological sample (or the gp120 proteins), washed and then the antibodies, (or a sample suspected of containing antibodies), applied. After washing to remove any non-bound ligand, a secondary binder moiety is added under suitable binding conditions, such that the secondary binder is capable of associating selectively with the bound ligand. The presence of the secondary binder can then be detected using techniques well known in the art. Typically, the secondary binder will comprise an antibody directed against the antibody ligands. A number of anti-human immunoglobulin (Ig) molecules are known in the art (e.g., commercially available goat anti-human Ig or rabbit anti-human Ig). Ig molecules for use herein will preferably be of the IgG or IgA type, however, IgM may also be appropriate in some instances. The Ig molecules can be readily conjugated to a detectable enzyme label, such as horseradish peroxidase, glucose oxidase, Beta-galactosidase, alkaline phosphatase and urease, among others, using methods known to those of skill in the art. An appropriate enzyme substrate is then used to generate a detectable signal.

In another embodiment, a "two antibody sandwich" assay can be used to detect the proteins of the present invention. In this technique, the solid support is reacted first with one or more of the antibodies directed against Env-CD4 mimetic complexes, washed and then exposed to the test sample. Antibodies are again added and the reaction visualized using either a direct color reaction or using a labeled second antibody, such as an anti-immunoglobulin labeled with horseradish peroxidase, alkaline phosphatase or urease.

Assays can also be conducted in solution, such that the viral proteins and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above.

The Env-CD4 complexes, produced as described above, or antibodies to the complexes, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

The CD4 mimetics, Env-CD4 mimetic complexes and antibodies thereto can also be used in vaccine compositions, individually or in combination, in e.g., prophylactic (i.e., to prevent infection) or therapeutic (to treat HIV following infection) vaccines. The vaccines can comprise mixtures of one or more of the modified Env proteins (or nucleotide sequences encoding the proteins), such as Env (e.g., gp120) proteins derived from more than one viral isolate. The vaccine may also be administered in conjunction with other antigens and immunoregulatory agents, for example, immunoglobulins, cytokines, lymphokines, and chemokines, including but not limited to IL-2, modified IL-2 (cys125-ser125), GM-CSF, IL-12, -interferon, IP-10, MIP1 and RANTES. The vaccines may be administered as polypeptides or, alternatively, as naked nucleic acid vaccines (e.g., DNA), using viral vectors (e.g., retroviral vectors, alphaviral vectors, adenoviral vectors, adeno-associated viral vectors) or non-viral vectors (e.g., liposomes, particles coated with nucleic acid or protein, including viral replicon particles). The vaccines may also comprise a mixture of protein and nucleic acid, which in turn may be delivered using the same or different vehicles. The vaccine may be given more than once (e.g., a "prime" administration followed by one or more "boosts") to achieve the desired effects. The same composition can be administered as the prime and as the one or more boosts. In another embodiment, different compositions can be used for priming and boosting.

A number of viral based systems have been developed for delivery and administration of nucleic acid molecules into mammalian cells. For example, retroviruses provide a convenient platform for nucleic acid delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, (1989) *BioTech.* 7:980-990; Miller, A. D., (1990) *Hum. Gene Ther.* 1:5-14; Scarpa, et al., (1991) *Virol.* 180:849-852; Burns, et al. (1993) *Proc. Natl. Acad. Sci. USA* 90:8033-8037; and Boris-Lawrie and Temin (1993) *Curr. Opin. Genet. Develop.* 3:102-109.

A number of adenovirus vectors have also been described. Unlike retroviruses which integrate into the host genome, adenoviruses persist extrachromosomally thus minimizing the risks associated with insertional mutagenesis (Haj-Ahmad and Graham, (1986) *J. Virol.* 57:267-274; Bett, et al., (1993) *J. Virol.* 67:5911-5921; Mittereder, et al., (1994) *Hum. Gene Ther.* 5:717-729; Seth, et al., (1994) *J. Virol.* 68:933-940; Barr, et al., (1994) *Gene Therapy* 1:51-58; Berkner, K. L., (1988) *BioTech.* 6:616-629; and Rich, et al., (1993) *Hum. Gene Ther.* 4:461-476).

Additionally, various adeno-associated virus (AAV) vector systems have been developed for nucleic acid delivery and administration. AAV vectors can be readily constructed using techniques well known in the art. See, e.g., U.S. Pat. Nos. 5,173,414 and 5,139,941; WO 92/01070; WO 93/03769;Lebkowski, et al. (1988) *Mol. Cell. Biol.* 8:3988-3996; Vincent, et al., (1990) *Vaccines* 90 (Cold Spring Harbor Laboratory Press); Carter, B. J., (1992) *Curr. Opin. Biotech.* 3:533-539; Muzyczka, N., (1992) *Curr. Top. Microbiol. Immunol.* 158: 97-129; Kotin, R. M., (1994) *Hum. Gene Ther.* 5:793-801; Shelling and Smith, (1994) *Gene Ther.* 1:165-169; and Zhou, et al., (1994) *J. Exp. Med.* 179:1867-1875.

Another vector system useful for delivering polynucleotides is the enterically administered recombinant poxvirus vaccines described by Small, Jr., P. A., et al. (U.S. Pat. No. 5,676,950).

Additional viral vectors which will find use for delivery and administration of nucleic acid molecules include those derived from the pox family of viruses, including vaccinia virus and avian poxvirus. In another embodiment, avipoxviruses, such as the fowlpox and canarypox viruses, can also be used for delivery of nucleic acid molecules. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael, et al., (1993) *J. Biol. Chem.* 268:6866-6869 and Wagner et al., (1992) *Proc. Nat Acad. Sci. USA* 89:6099-6103, can also be used for nucleic acid delivery or administration.

Members of the Alphavirus genus, such as, but not limited to, vectors derived from the Sindbis, Semliki Forest, and Venezuelan Equine Encephalitis viruses, will also find use as viral vectors for delivery and administration of nucleic acid molecules. For a description of Sindbis-virus derived vectors see, e.g., Dubensly, et al., (1996)*J. Virol.* 70:508-519; WO 95/07995; WO 96/17072; U.S. Pat. No. 5,843,723; and U.S. Pat. No. 5,789,245. See also WO 02/099035; and U.S. Publication No. 2003/018262.

Viral replicon particles can be used for delivery and administration of nucleic acid and polypeptide molecules. For example, alphavirus replicon particles, including chimeric alphavirus replicon particles, can be used for delivery and administration of nucleic acid and polypeptide molecules. For a description of alphavirus replicon particle systems see, e.g., WO 02/099035; U.S. Publication No. 2003/018262; WO 96/37616; U.S. Publication No. 2003/0119182; WO 03/023026; and WO 05/016961.

Nucleic acid and polypeptide molecules can also be delivered without a viral vector. For example, nucleic acid and/or polypeptide molecules can be packaged in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, (1991) *Biochim. Biophys. Acta.* 1097:1-17; Straubinger, et al., (1983), *Meth. Enzymol* 101:512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner, et al., (1987) *Proc. Natl. Acad. Sci. USA* 84:7413-7416); mRNA (Malone, et al., (1989) *Proc. Natl. Acad. Sci. USA* 86:6077-6081); and purified transcription factors (Debs, et al., (1990) *J. Biol. Chem.* 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner, et al., (1987) *Proc. Natl. Acad. Sci. USA* 84:7413-7416). Other commercially available lipids include (DDAB/DOPE) and DOTAP/DOPE (Boerhinger). Other cationic liposomes can be prepared from readily available materials using techniques well known in the art. See, e.g., Szoka, et al., (1978) *Proc. Natl. Acad. Sci. USA* 75:4194-4198; WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger, et al., (1983) *Meth. Immunol.* 101:512-527; Szoka, et al., (1978) *Proc. Natl. Acad. Sci. USA* 75:4194-4198; Papahadjopoulos, et al., (1975) *Biochim. Biophys. Acta* 394:483-491; Wilson, et al., (1979) *Cell* 17:77-84); Deamer and Bangham, (1976) *Biochim. Biophys. Acta* 443:629-634; Ostro, et al., (1977) *Biochim. Biophys. Res. Commun.* 76:836-842; Fraley, et al., (1979) *Proc. Natl. Acad. Sci. USA* 76:3348-3352); Enoch and Strittmatter, (1979) *Proc. Natl. Acad. Sci. USA* 76:145-149; Fraley, et al., (1980) *J. Biol. Chem.* 255: 10431-10435; Szoka and Papahadjopoulos, (1978) *Proc. Natl. Acad. Sci. USA* 75:4194-4198; and Schaefer-Ridder, et al., (1982) *Science* 215:166-168.

The nucleic acid and/or polypeptide molecules can also be delivered in cochleate lipid compositions similar to those described by Papahadjopoulos, et al., (1975) *Biochim. Biophys. Acta.* 394:483-491. See, also, U.S. Pat. Nos. 4,663,161 and 4,871,488.

The nucleic acid and/or polypeptide molecules may also be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery, et al., (1993) *Pharm. Res.* 10:362-368; McGee, J P, et al., (1997) *J. Microencapsul.* 14(2):197-210; O'Hagan D T, et al., (1993) *Vaccine* 11(2):149-154. Suitable microparticles may also be manufactured in the presence of charged detergents, such as anionic or cationic detergents, to yield microparticles with a surface having a net negative or a net positive charge. For example, microparticles manufactured with anionic detergents, such as hexadecyltrimethylammonium bromide (CTAB), i.e. CTAB-PLG microparticles, adsorb negatively charged macromolecules, such as DNA (see, e.g., WO 00/06123).

The vaccines will generally include one or more "pharmaceutically acceptable excipients or vehicles" such as water, saline, glycerol, ethanol, etc. Exemplary excipients also include, without limitation, those selected from the group consisting of carbohydrates, inorganic salts, antimicrobial agents, antioxidants, surfactants, buffers, acids, bases, and combinations thereof Additionally, auxiliary substances, such as wetting or emulsifying agents, pH buffering substances, and the like, may be present in such vehicles. These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the Env polypeptide may be conjugated to a bacterial toxoid, such as toxoid from diphtheria, tetanus, cholera, etc.

Adjuvants may also be used to enhance the effectiveness of the vaccines. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. W093/13202 and W092/19265); (7) MF59-CpG, (8) PLG-CpG, and (9) other substances that act as immunostimulating agents to enhance the effectiveness of the composition.

Muramyl peptides include, but are not limited to, N-acetyl-murainyl-L-threonyl-D-isoglutamine (thr-MDP), N-acetyl-normuramyl-L-alanyl-D-isogluatme (nor-MDP), N-acetyl-muramyl-L-alanyl-D-isogluatminyl-L-alanine-2-(1'-2'-dipalmitoyl-sn-glyccero-3-huydroxyphosphoryloxy)-ethylamine (MTP-PE), etc.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the compositions described herein (complexes, mimetics, antibodies) can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The vaccines will comprise a therapeutically effective amount of the Env-CD4 mimetic complexes, or further complexes of these complexes, or antibodies directed to these complexes and any other of the above-mentioned components, as needed. By "therapeutically effective amount" is meant an amount of a CD4 mimetic-complexed Env (e.g., gp120) protein that will induce a protective immunological response in the uninfected, infected or unexposed individual to whom it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell.

Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular Env-CD4 complex selected and its mode of administration, among other factors. An appropriate effective amount can be readily determined by one of skill in the art. A "therapeutically effective amount" will fall in a relatively broad range that can be determined through routine trials.

CD4 mimetics, complexes and antibodies can be injected or otherwise administered either subcutaneously, epidermally, intradermally, intramucosally such as nasally, rectally and vaginally, intraperitoneally, intravenously, orally or intramuscularly. Other modes of administration include oral and pulmonary administration, suppositories, needle-less injection, transcutaneous and transdermal applications. Dosage treatment may be a single dose schedule or a multiple dose schedule. Administration may also be combined with administration of peptides or other substances.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXAMPLES

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Rational Design of CD4 Mimetics

Small molecules that act as CD4 mimetics as described herein were obtained as follows. In a first step, based on known information about CD4 and CD4 mimetic, CD4M33 (Martin et al. (2003) *Nat Biotechnol.* 21(1):71-76), an in-house library of small molecules was examined for compounds exhibiting structural similarity to CD4M33. Approximately 100 compounds were identified in this first preliminary screening step.

In a second step, each of the 100 structurally identified compounds was screened for its ability to compete with CD4 binding to Env (gp120) as well as its ability to induce the desired conformational change in the HIV Env protein to expose inducible epitopes. Both binding competition and exposure of cryptic epitopes were analyzed using Biacore's SRP systems. (Biacore Inc., Piscataway, N.J.), following the manufacturer's instructions.

As illustrated graphically in FIG. 1, compound 5 (ethyl 1-[(4,6-dimethyl-1H-indol-2-yl)carbonyl]piperidine-4-carboxylate) inhibited binding of Env to the CD4 chip in comparison to when the small molecule was not present, indicating that the small molecule 5 competed with the CD4 on the chip to bind to the Env protein.

Figure 2:
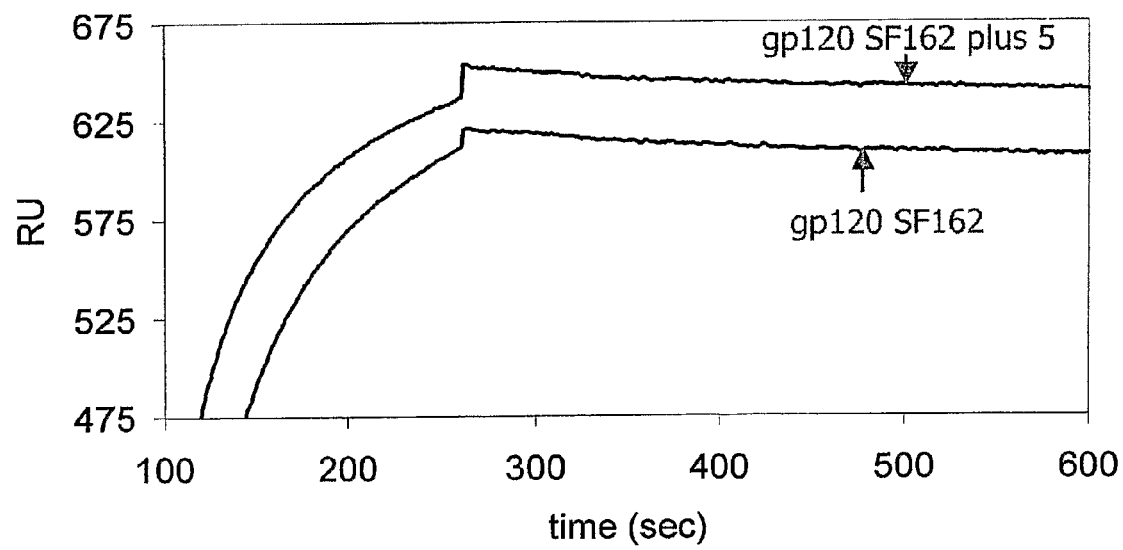
FIG. 2 is a graph depicting upregulation in binding of monoclonal antibody 17b (MAb 17b) to an illustrative CD4 mimetic-Env complex of the invention in comparison to binding to a sCD4-gp120 SMF162 complex (Examples 1 and 4). Monoclonal 17b recognizes an epitope that is exposed upon binding of Env to CD4.
Figure 4A:
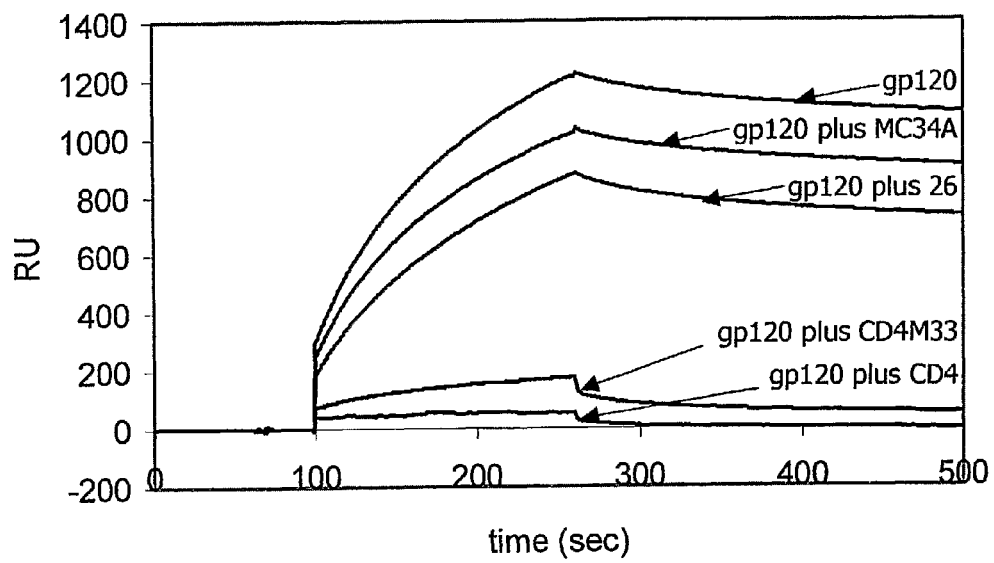
FIGS. 4A and 4B are graphs demonstrating the inhibition of CD4 binding to gp120 and the upregulation of CD4 inducible epitopes on gp120, respectively, for an illustrative small molecule CD4 mimetic of the invention, 26, 2-[4-(2-methoxy-phenyl)-piperazin-1-yl]-1-(2-methyl-1H-indol-3-yl)-ethanone (Example 6)
Figure 4B:
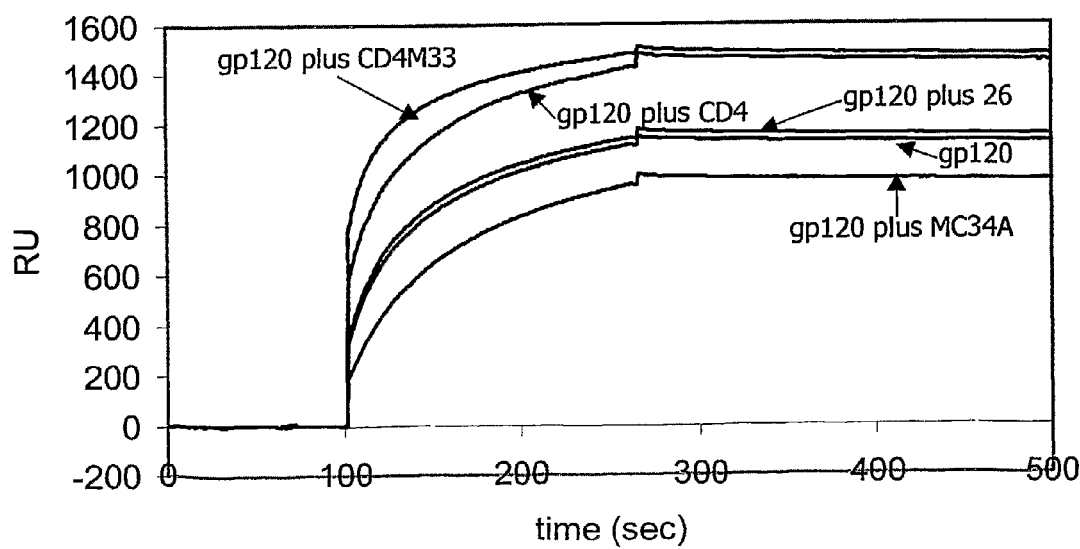
Figure 5A:
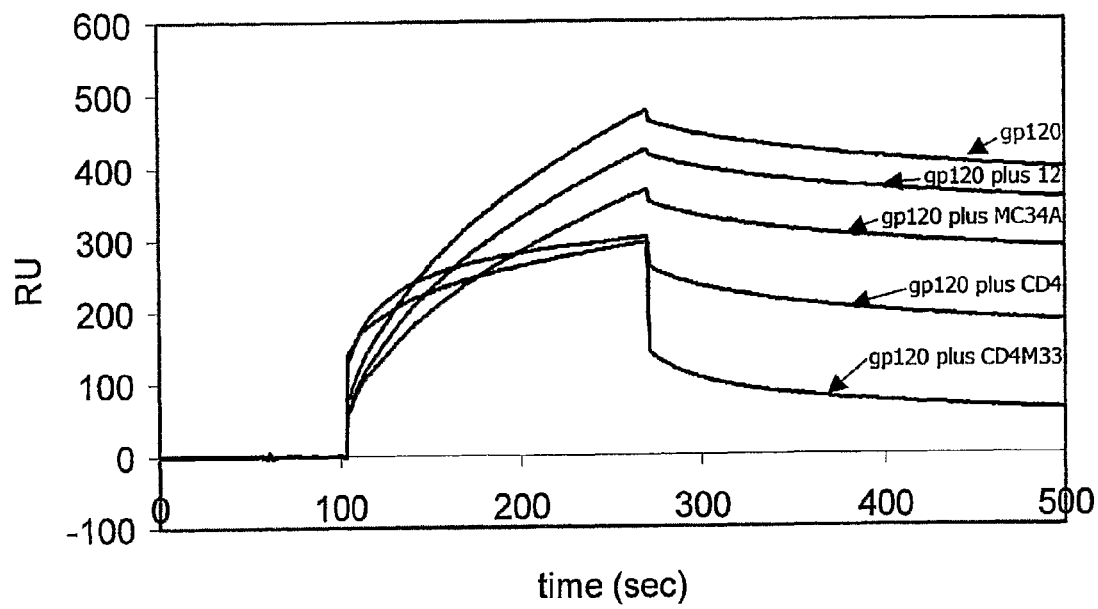
FIGS. 5A and 5B are graphs illustrating the inhibition of CD4 binding to gp120, and the absence of upregulation of CD4 inducible epititopes on gp120, respectively, for an illustrative small molecule CD4 mimetic of the invention, 12, [4-(1H-indol-3-yl)-piperidin-1-yl]-(3,4,5-trimethoxy-phenyl)-methanone (Example 6)
Figure 5B:
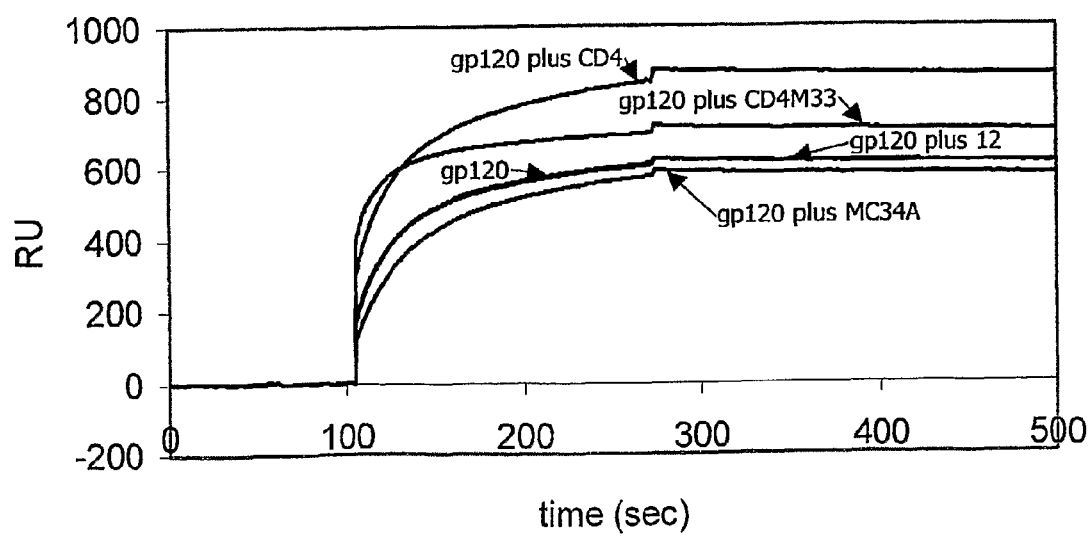
Figure 6A:
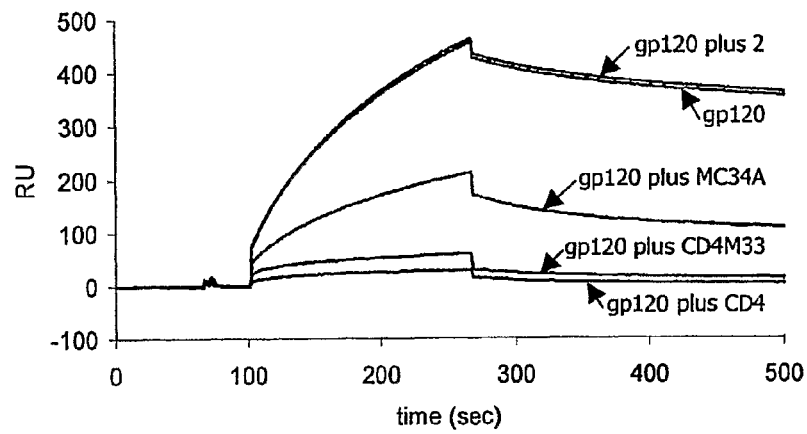
FIGS. 6A, 6B, and 6C are graphs illustrating the non-inhibition of CD4 binding to gp120 (FIG. 6A), and the upregulation of CD4 inducible epitopes on gp120 as indicated by extent of binding to the monoclonal antibodies 17b (FIG. 6B) and 48D (FIG. 6C), respectively, for an illustrative small molecule CD4 mimetic of the invention, 2, 2-(4-benzylpiperazin-1-yl)-1-(5-methoxy-1H-indol-3-yl)ethanone.
Figure 6B:
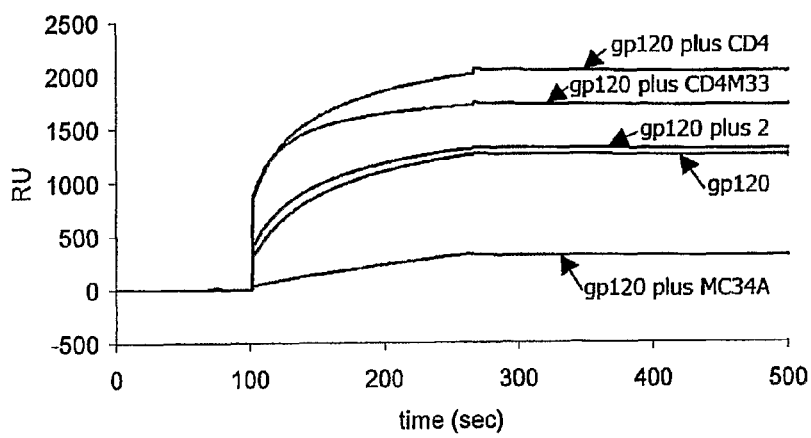
Figure 6C:
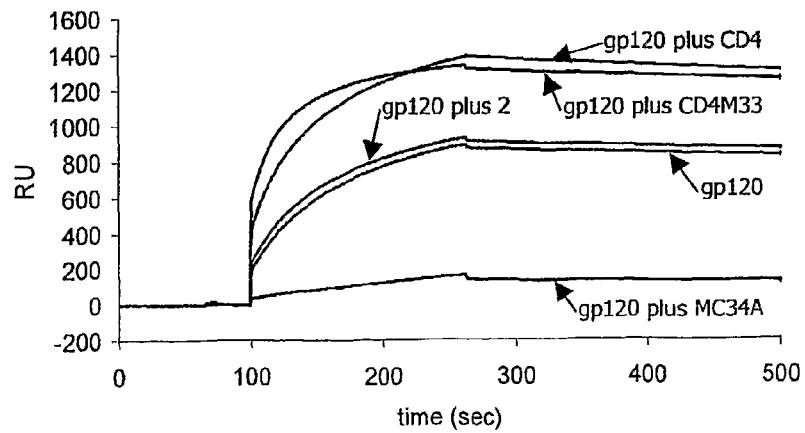

Similarly, FIG. 2 illustrates that a complex of Env and small molecule 5 exhibited enhanced binding to monoclonal antibody 17b in comparison to known Env-sCD4 complexes (see Example 4 which follows). Illustrative CD4 mimetic, 5, both competes with CD4 for binding to cryptic epitopes on Env and upregulates binding to mAB 17b.

Thus, small molecule CD4 mimetics such as those described herein induce a conformational transformation of oligomeric (o-gp140) envelopes to thereby unmask cryptic epitopes close to co-receptor sites in the gp120 subunit and efficiently increase co-receptor binding affinity in different gp120 envelopes.

Example 2

Unmasking Crytic Epitopes pf GP41 Subunit in Oligomeric Envelopes

The CD4 mimetics identified as described above are also tested for their ability to induce a conformational transformation to expose cryptic epitopes in oligomeric Env structures using SPR technology (Example 1) with 2F5 mAb or DP178 peptides (or congeners).

In instances in which Biacore screening indicates that gp41 epitopes are exposed upon binding of particular CD4 mimetics as described herein to oligomeric Env proteins, multiple mimetics may then be coupled to produce novel bi-functional ligands, presenting increased potency in unmasking Env (gp41) epitopes. Novel chimeric oligomeric envelopes, complexed to such bi-functional ligand mimetics are also produced and tested. Candidate envelope proteins with superior exposure of gp120 and gp41 cryptic epitopes are subsequently tested in animals for the induction of neutralizing antibodies.

Example 3

Production of Monoclonal Antibodies Targeting Cryptic Conserved Epitopes of env

Selected Env-CD4 mimetic complex immunogens are injected in rats or mice to prepare monoclonal antibodies according to standard procedures. Clones are screened in ELISA against CD4 miniprotein-gp120 complex, CD4 miniprotein-o-gp41, gp 120 and o-gp41 alone and CD4 M33 mimetic as well. Clones exhibiting highest affinity for complexes as compared to envelopes alone are further tested in Biacore, as described in Example 1. Clones scoring positive in Biacore against the CD4M33-gp120 and or CD4M33-o-gp140 complexes are selected and used for bulk production of ascites fluids.

Example 4

Production of Monoclonal Antibodies Targeting Cryptic Conserved Epitopes of env

Surface plasmon resonance assays were performed using a BIACORE 3000 optical biosensor system (Biacore AB, Uppsala, Sweden) with simultaneous monitoring of relevant flow cells. To perform the kinetic study of the binding of HIV env to sCD4, sCD4 was immobilized using amine coupling onto CM5 sensor chip to attain 4000 response units. To perform the kinetic study of the binding of HIV env to the monoclonal antibody 17b, antibodies were immobilized using amine coupling onto a CM5 sensor chip to attain 2000 response units. Using PBS buffer (pH 7.4) with 0.05% Tween 20 and 3% DMSO, association was assessed by passing gp120SF162 (GenBank P03378; Sanchez-Pescador et al. (1985) *Science*, 227(4686): 484-492), with and without various controls or small molecules, over the chip surface at a flow rate of 25 μl/min. The concentration of gp120SMF162 used was 1 uM for all samples. As a negative control, a control surface coupled to 2000 response units of BSA (Pierce) was used. A buffer only control was subtracted from all sensograms. Responses were measured by assessing the maximum RUs (response units) obtained at the peak of the binding curve.

The percentage upregulation of 17b was determined by dividing the peak RU observed for the Env polypeptide/compound complex divided by the peak RU for the Env polypeptide alone.

The following compounds in the table below were found to exhibit at least a 1% upregulation of 17b.

TABLE 1

| Compound | Structure | Name |
|---|---|---|
| 1 | 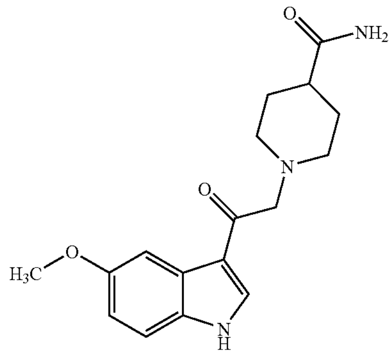 | 1-[2-(5-methoxy-1H-indol-3-yl)-2-oxoethyl]piperidine-4-carboxamide |
| 2 | 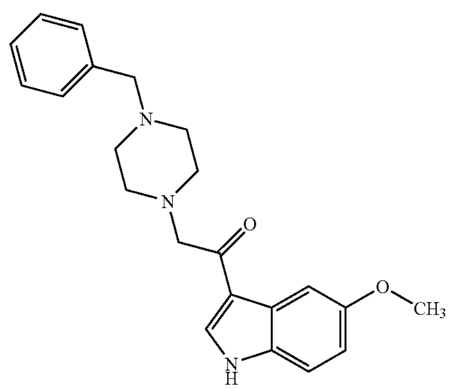 | 2-(4-benzylpiperazin-1-yl)-1-(5-methoxy-1H-indol-3-yl)ethanone |
| 3 | 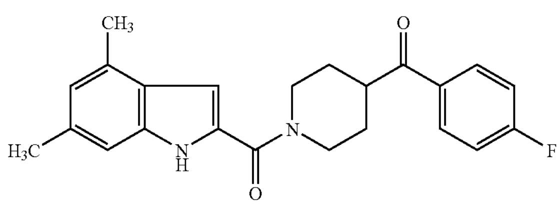 | {1-[(4,6-dimethyl-1H-indol-2-yl)carbonyl]piperidin-4-yl}(4-fluorophenyl)methanone |
| 4 | 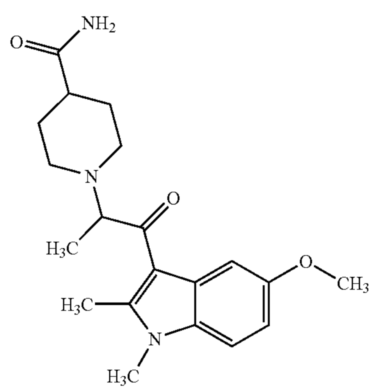 | 1-[2-(5-methoxy-1,2-dimethyl-1H-indol-3-yl)-1-methyl-2-oxoethyl]piperidine-4-carboxamide |
| 5 | 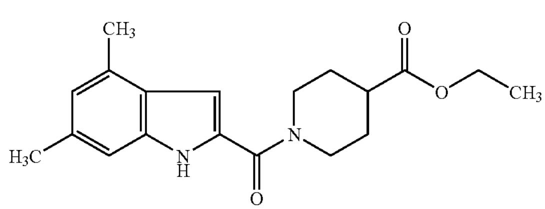 | ethyl 1-[(4,6-dimethyl-1H-indol-2-yl)carbonyl]piperidine-4-carboxylate |

TABLE 1-continued

| Compound | Structure | Name |
| --- | --- | --- |
| 6 | 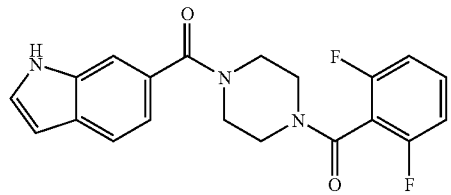 | 6-{[4-(2,6-difluorobenzoyl)piperazin-1-yl]carbonyl}-1H-indole |
| 7 | 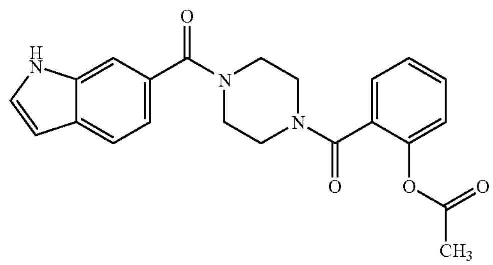 | 2-{[4-(1H-indol-6-ylcarbonyl)piperazin-1-yl]carbonyl}phenyl acetate |
| 8 | 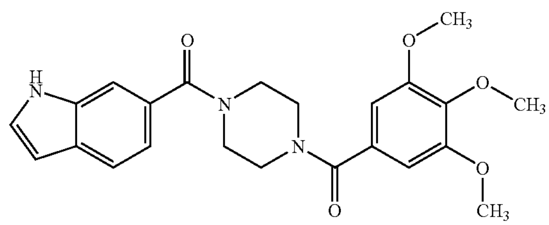 | 6-{[4-(3,4,5-trimethoxybenzoyl)piperazin-1-yl]carbonyl}-1H-indole |
| 9 | 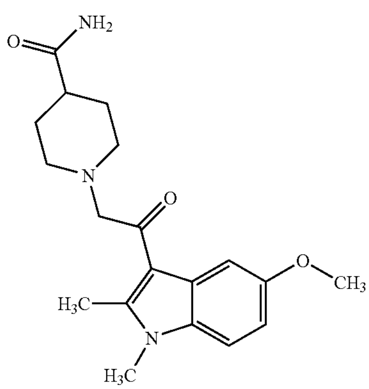 | 1-[2-(5-methoxy-1,2-dimethyl-1H-indol-3-yl)-2-oxoethyl]piperidine-4-carboxamide |
| 10 | 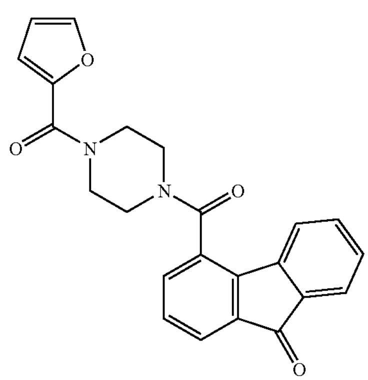 | 4-{[4-(2-furoyl)piperazin-1-yl]carbonyl}-9H-fluoren-9-one |

Example 5

Neutralizing Antibody Production Using Small Molecule Cb4 Mimetics of CD4 Mimetic-env Complexes Rabbits Groups of 4-5 or more rabbits each are immunized with small molecule CD4 mimetics and/or complexes of Env-CD4 mimetics at 0, 4, 12 and 24 weeks. Sera are collected biweekly and analyzed against, e.g., SF2 or SF162 gp120 in an ELISA. The results from these rabbit studies will reveal which animals mount a strong immune response against gp120.

Monkeys

Groups of 5 or more monkeys are immunized with CD4 mimetics and/or Env-CD4 mimetic complexes with adjuvant along with control groups of Env protein. Complexes and are made with monomeric and oligomeric forms of SF162 Env with and without V2-deletes and the antibody responses compared. Immunization schedules are at 0, 4, and 24 week immunizations. When warranted, an additional booster may be included at later time points

Example 6

Additional Screening of Small Molecule CD4 Mimetics for CD4 Binding Inhibition and/or Upregulation of CD4 Inducible Epitopes Additional candidate small molecules were screened for CD4 binding inhibition and upregulation of CD4 inducible epitopes, e.g., mAbs 17b and 48D, by HPLC and BIAcore methods as described in Examples 1 and 4 above. Each of the compounds in Table 5 below was screened three times by both methods using different lots of both gp120 and antibodies. The rounds of screening tests were additionally carried out on different dates.

CD4 binding competition was examined in the free solution state by HPLC. Various candidate small molecules were each mixed with gp120SF162 and the resulting solution was incubated for 1 hour at 37° C. Fluorescently-labelled CD4, CD4 488, was then added to each incubated solution, and the resulting mixture was analyzed by size exclusion HPLC (SEC-HPLC), using fluorescent signal detection. The extent of competition with CD4 was determined as follows. For small molecule candidate samples in which the fluorescent signal was lower than the fluorescent signal of the control (gp120 alone), the small molecule was determined to exhibit competitive binding with CD4. For small molecule candidate samples in which the fluorescent signal was essentially unchanged or normal relative to the control, the small molecule was determined to exhibit no competitive binding with CD4, i.e., the small molecule candidate was not classified as an inhibitor of CD4-binding to Env.

Based upon these additional screening studies, numerous small molecule CD4 mimetics were identified. In sum, three different classes of small molecule CD4 mimetics were identified: (i) molecules that inhibit CD4 binding, (ii) molecules that upregulate CD4 inducible epitopes (17b and 48D), and (iii) molecules that both inhibit CD4 binding and upregulate CD4 inducible epitopes.

Tables 2-4 below demonstrate the chemical structures and molecular weights of representative small molecule CD4 mimetics, classified according to their CD4-inhibitory binding capability as well as their ability to upregulate certain CD4 inducible epitopes.

Supporting screening data for illustrative small molecule CD4 mimetics in accordance with the invention is presented as FIG. 3.

TABLE 2

Compounds that inhibit (compete with) CD4 but do not upregulate 17b.

| Compound | Structure | Name | Mol Formula | MW |
|---|---|---|---|---|
| 11 |  | 1-[4-(1H-indole-6-carbonyl)-piperazin-1-yl]-2,2-diphenyl-ethanone | $C_{27}H_{25}N_3O_2$ | 423.5 |
| 8 |  | [4-(1H-indole-6-carbonyl)-piperazin-1-yl]-(3,4,5-trimethoxy-phenyl)-methanone | $C_{23}H_{25}N_3O_5$ | 423.5 |

TABLE 2-continued

Compounds that inhibit (compete with) CD4 but do not upregulate 17b.

| Compound | Structure | Name | Mol Formula | MW |
|---|---|---|---|---|
| 12 | 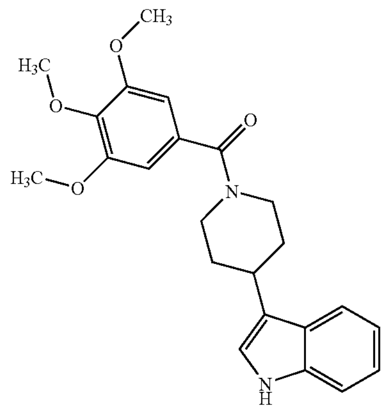 | [4-(1H-indol-3-yl)-piperidin-1-yl]-(3,4,5-trimethoxy-phenyl)-methanone | $C_{23}H_{26}N_2O_4$ | 394.5 |
| 13 | 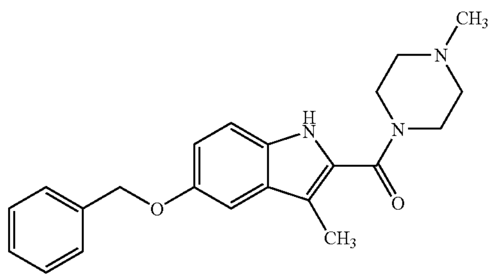 | (5-Benzyloxy-3-methyl-1H-indol-2-yl)-(4-methyl-piperazin-1-yl)-methanone | $C_{22}H_{25}N_3O_2$ | 363.5 |
| 14 | 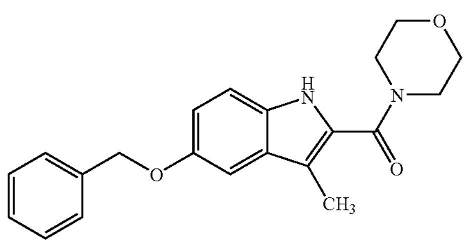 | (5-Benzyloxy-3-methyl-1H-indol-2-yl)-morpholin-4-yl-methanone | $C_{21}H_{22}N_2O_3$ | 350.4 |
| 15 | 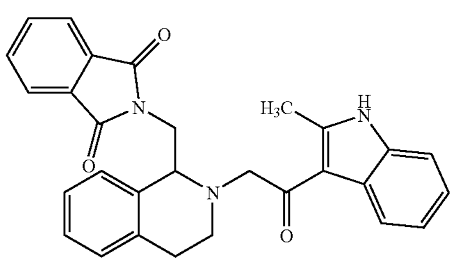 | 2-{2-[2-(2-Methyl-1H-indol-3-yl)-2-oxo-ethyl]-1,2,3,4-tetrahydro-isoquinolin-1-ylmethyl}-isoindole-1,3-dione | $C_{29}H_{25}N_3O_3$ | 463.5 |
| 16 | 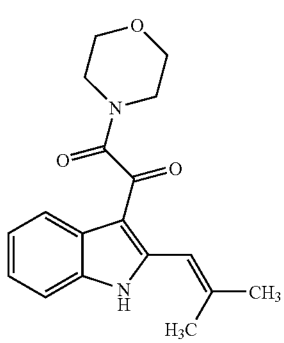 | 1-[2-(2-Methyl-propenyl)-1H-indol-3-yl]-2-morpholin-4-yl-ethane-1,2-dione | $C_{18}H_{20}N_2O_3$ | 312.4 |

TABLE 2-continued

Compounds that inhibit (compete with) CD4 but do not upregulate 17b.

| Compound | Structure | Name | Mol Formula | MW |
|---|---|---|---|---|
| 17 | 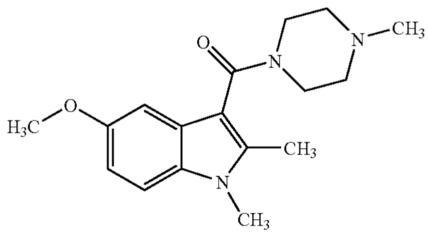 | (5-Methoxy-1,2-dimethyl-1H-indol-3-yl)-(4-methyl-piperazin-1-yl)-methanone | $C_{17}H_{23}N_3O_2$ | 301.4 |
| 18 | 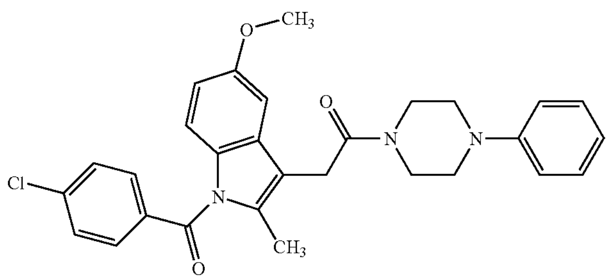 | 2-[1-(4-Chloro-benzoyl)-5-methoxy-2-methyl-1H-indol-3-yl]-1-(4-phenyl-piperazin-1-yl)-ethanone | $C_{29}H_{28}ClN_3O_3$ | 502.0 |

TABLE 3

Compounds that upregulate 17b but do not inhibit (compete with) CD4.

| Compound | Structure | Name | Mol Formula | MW |
|---|---|---|---|---|
| 2 | 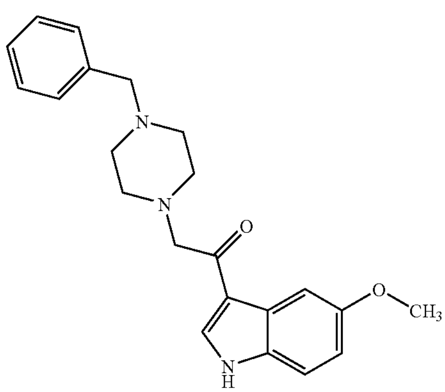 | 2-(4-Benzyl-piperazin-1-yl)-1-(5-methoxy-1H-indol-3-yl)-ethanone | $C_{22}H_{25}N_3O_2$ | 363.5 |
| 20 | 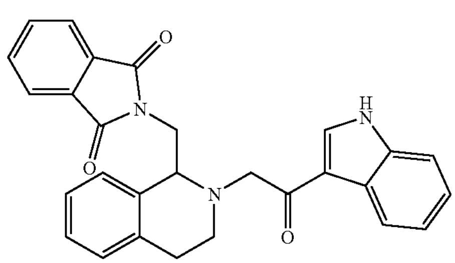 | 2-{2-[2-(1H-indol-3-yl)-2-oxo-ethyl]-1,2,3,4-tetrahydro-isoquinolin-1-ylmethyl}-isoindole-1,3-dione | $C_{28}H_{23}N_3O_3$ | 449.5 |

TABLE 3-continued
Compounds that upregulate 17b but do not inhibit (compete with) CD4.
| Compound | Structure | Name | Mol Formula | MW |
|---|---|---|---|---|
| 21 | 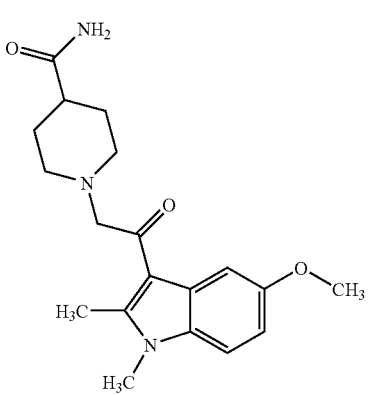 | 1-[2-(5-Methoxy-1,2-dimethyl-1H-indol-3-yl)-2-oxo-ethyl]-piperidine-4-carboxylic acid amide | $C_{19}H_{25}N_3O_3$ | 343.4 |
| 22 | 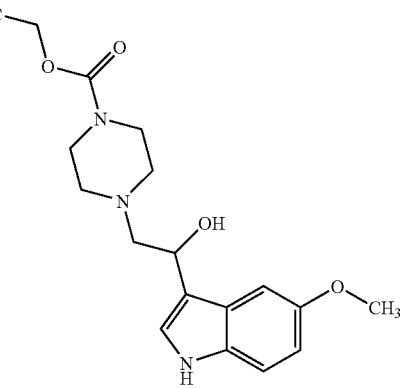 | 4-[2-Hydroxy-2-(5-methoxy-1H-indol-3-yl)-ethyl]-piperazine-1-carboxylic acid ethyl ester | $C_{18}H_{25}N_3O_4$ | 347.4 |
| 23 | 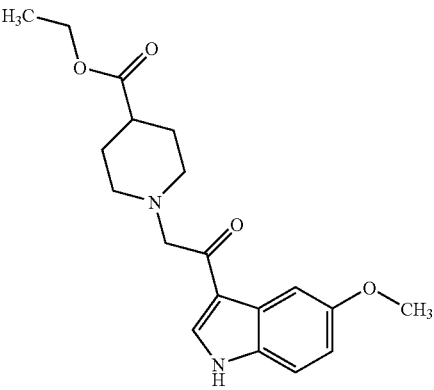 | 1-[2-(5-Methoxy-1H-indol-3-yl)-2-oxo-ethyl]-piperidine-4-carboxylic acid ethyl ester | $C_{19}H_{24}N_2O_4$ | 344.4 |

TABLE 4

| Compound | Structure | Name | Mol Formula | MW |
|---|---|---|---|---|
| | Compounds that inhibit (compete with) CD4 and upregulate 17b. | | | |
| 19 | 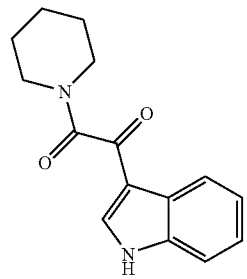 | 1-(1H-indol-3-yl)-2-piperidin-1-yl-ethane-1,2-dione | $C_{15}H_{16}N_2O_2$ | 256.3 |
| 20 | 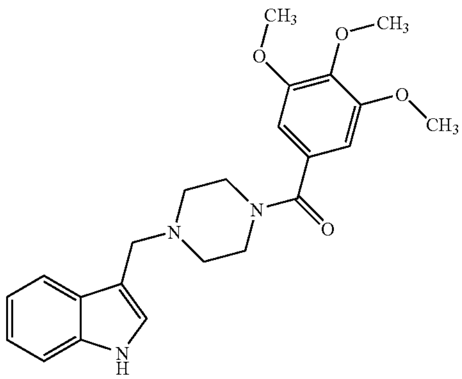 | [4-(1H-indol-3-ylmethyl)-piperazin-1-yl]-(3,4,5-trimethoxy-phenyl)-methanone | $C_{23}H_{27}N_3O_4$ | 409.5 |
| 21 | 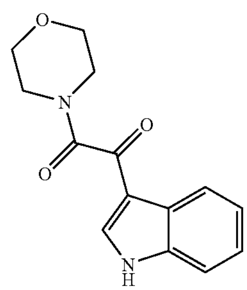 | 1-(1H-indol-3-yl)-2-morpholin-4-yl-ethane-1,2-dione | $C_{14}H_{14}N_2O_3$ | 258.3 |
| 22 | 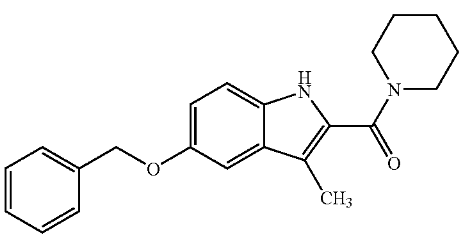 | (5-Benzyloxy-3-methyl-1H-indol-2-yl)-piperidin-1-yl-methanone | $C_{22}H_{24}N_2O_2$ | 348.4 |
| 23 | 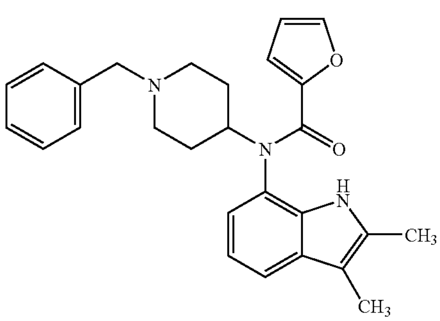 | Furan-2-carboxylic acid (1-benzyl-piperidin-4-yl)-(2,3-dimethyl-1H-indol-7-yl)-amide | $C_{27}H_{29}N_3O_2$ | 427.5 |

TABLE 4-continued

Compounds that inhibit (compete with) CD4 and upregulate 17b.

| Compound | Structure | Name | Mol Formula | MW |
|---|---|---|---|---|
| 24 | 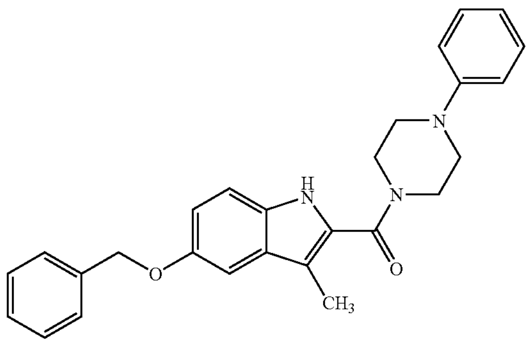 | (5-Benzyloxy-3-methyl-1H-indol-2-yl)-(4-phenyl-piperazin-1-yl)-methanone | $C_{27}H_{27}N_3O_2$ | 425.5 |
| 25 | 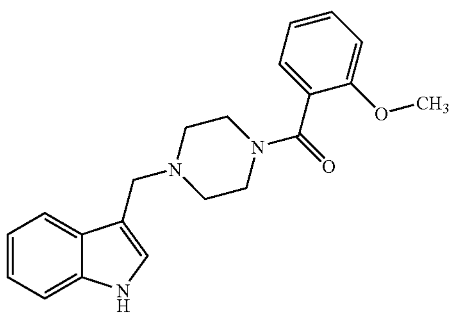 | [4-(1H-indol-3-ylmethyl)-piperazin-1-yl]-(2-methoxy-phenyl)-methanone | $C_{21}H_{23}N_3O_2$ | 349.4 |
| 26 | 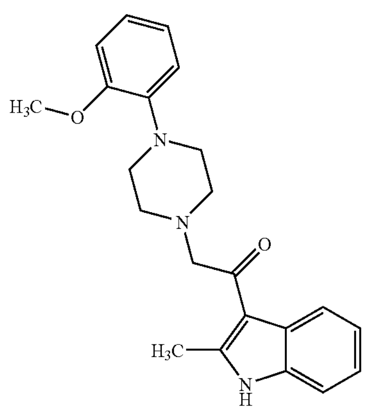 | 2-[4-(2-Methoxy-phenyl)-piperazin-1-yl]-1-(2-methyl-1H-indol-3-yl)-ethanone | $C_{22}H_{25}N_3O_2$ | 363.5 |
| 27 | 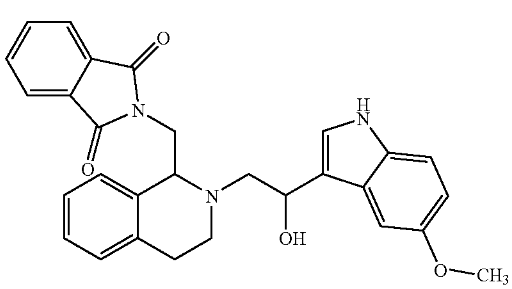 | 2-{2-[2-Hydroxy-2-(5-methoxy-1H-indol-3-yl)-ethyl]-1,2,3,4-tetrahydro-isoquinolin-1-ylmethyl}-isoindole-1,3-dione | $C_{29}H_{27}N_3O_4$ | 481.5 |

TABLE 4-continued

Compounds that inhibit (compete with) CD4 and upregulate 17b.

| Compound | Structure | Name | Mol Formula | MW |
|---|---|---|---|---|
| 28 | 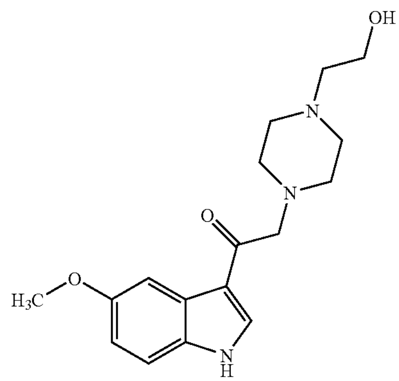 | 2-[4-(2-Hydroxy-ethyl)-piperazin-1-yl]-1-(5-methoxy-1H-indol-3-yl)-ethanone | $C_{17}H_{23}N_3O_3$ | 317.4 |
| 29 | 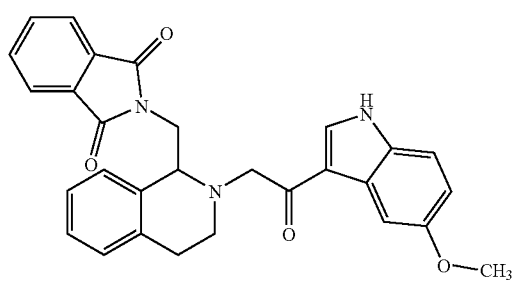 | 2-{2-[2-(5-Methoxy-1H-indol-3-yl)-2-oxo-ethyl]-1,2,3,4-tetrahydro-isoquinolin-1-ylmethyl}-isoindole-1,3-dione | $C_{29}H_{25}N_3O_4$ | 479.5 |
| 30 | 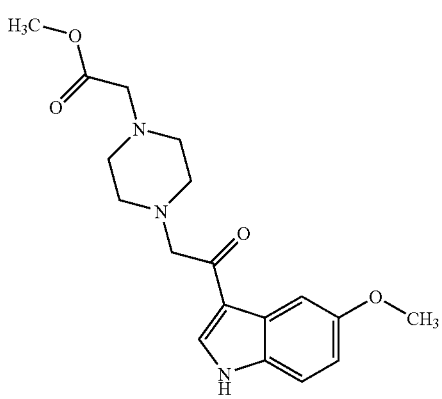 | {4-[2-(5-Methoxy-1H-indol-3-yl)-2-oxo-ethyl]-piperazin-1-yl}-acetic acid methyl ester | $C_{18}H_{23}N_3O_4$ | 345.4 |
| 1 | 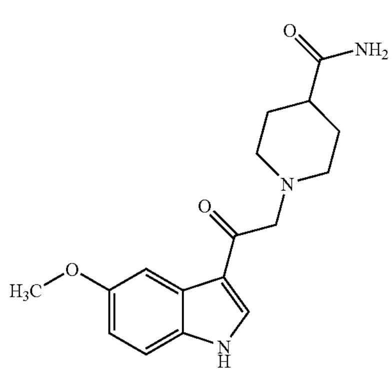 | 1-[2-(5-methoxy-1H-indol-3-yl)-2-oxoethyl]piperidine-4-carboxamide | | |

TABLE 4-continued

Compounds that inhibit (compete with) CD4 and upregulate 17b.

| Compound | Structure | Name | Mol Formula | MW |
|---|---|---|---|---|
| 2 | 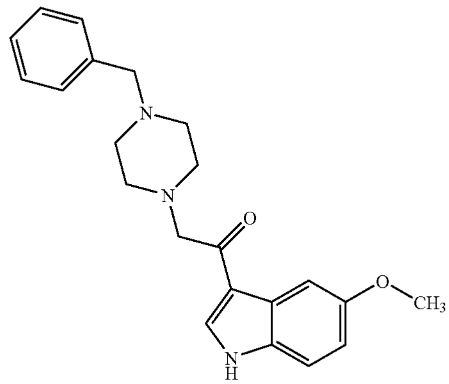 | 2-(4-benzylpiperazin-1-yl)-1-(5-methoxy-1H-indol-3-yl)ethanone | | |
| 3 | 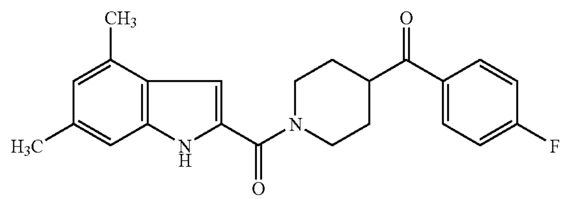 | {1-[(4,6-dimethyl-1H-indol-2-yl)carbonyl]piperidin-4-yl}(4-fluorophenyl)methanone | | |
| 4 | 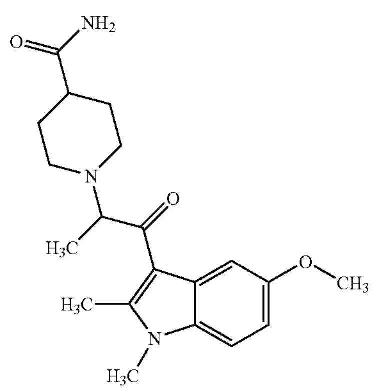 | 1-[2-(5-methoxy-1,2-dimethyl-1H-indol-3-yl)-1-methyl-2-oxoethyl]piperidine-4-carboxamide | | |
| 5 | 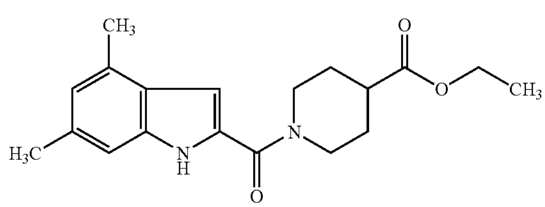 | ethyl 1-[(4,6-dimethyl-1H-indol-2-yl)carbonyl]piperidine-4-carboxylate | | |
| 6 | 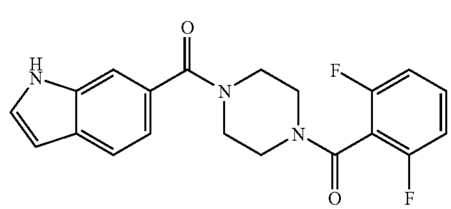 | 6-{[4-(2,6-difluorobenzoyl)piperazin-1-yl]carbonyl}-1H-indole | | |

TABLE 4-continued

Compounds that inhibit (compete with) CD4 and upregulate 17b.

| Compound | Structure | Name | Mol Formula | MW |
|---|---|---|---|---|
| 7 | 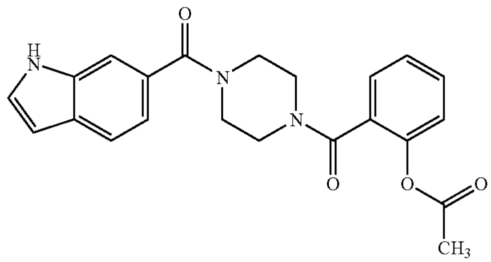 | 2-{[4-(1H-indol-6-ylcarbonyl)piperazin-1-yl]carbonyl}phenyl acetate | | |
| 8 | | 6-{[4-(3,4,5-trimethoxybenzoyl)piperazin-1-yl]carbonyl}-1 responses will primarily be measured by enumerating the number of CD4+ and CD8+ T cells that secrete IFN-γ in response to specific peptides. If particular (matching) MHC specific tetramer reagents are not available, then the majority of assays will by performed by CD8+ ELISpot assays with overlapping pools of peptides, from which epitope specificities are determined. Classical bulk lysis (Chromium release) assays are performed as confirmatory assays. Additional supplementary assays such as flow cytometric assays to measure antigen-specific intracellular cytokines in T-cell subsets, and tetramer analysis to measure antigen-specific CD8+ T-cell populations in animals with MHC specificities that match available tetramers will also be performed on a subset of animals.

Assays for the measurement of cellular immune responses in the mucosal will include ELISpot, measurements of antibody-secreting cells (ASC), and FACS analysis of antigen-specific intracellular cytokines in mucosal T-cells.

B. Humoral/Neutralizing Antibody Responses

Antibody responses and neutralization assays are performed as described above and/or samples are sent to outside vendor for evaluation (e.g., Virologic, Inc).

C. Measurements of Vaccine Efficacy Post-Challenge

The Env-CD4 mimetics complexes that give strong and broad neutralization, complemented by strong CD4 and CD8 T cell responses, are tested by homologous and heterologous systemic (IV) and mucosal (IR) challenges. Over the last ten years this has proven to be the most reliable challenge dose where protection can be achieved with all controls contacting disease. Challenge is performed 8 weeks after the final immunization, except during the final year of study when challenges are performed in parallel groups of monkeys when half of the designated groups are challenged at 8 months after the final immunization.

The post-challenge measurements of vaccine efficacy to be evaluated are summarized in Table 5. The plasma and PBMC are collected for analysis (e.g., virological and FACS) at two-week intervals for the first two months after challenge and at monthly intervals thereafter.

Plasma virus load analysis is performed as well as a detailed analysis of any persistent low copy proviral infection of PBMC or lymph node cells. Detailed FACS analysis provide evidence of T-cell activation and/or CD4+ T cell loss and disease progression. Immunoblot assays and ELISA for non-vaccine viral antigens are used to determine whether seroconversion has occurred.

Protected animals are identified after taking all these parameters into account. "Protection against infection" is defined as no indication of virus infection by any of the virologic (and serologic) sensitive assays listed in Table 5. "Partial protection" is defined by significant reductions in the virus load as measured by quantitative virus isolation, levels of viral RNA, frequency of detection of proviral DNA in PBMC and lymph nodes (LN). "Protection from disease" is defined primarily by reductions in the decline of CD4+ T cells, fewer or less severe signs and symptoms, survival, and secondarily, by reductions in virus load, and the robustness of the post-challenge immune responses.

TABLE 5

Post-Challenge Measurements of Vaccine Efficacy

| Measurements of Virus Load | Immune Status/Disease Progression |
|---|---|
| Plasma RNA (quantitative PCR) | FACS (CD3, CD4, CD8, CD16, HLA-DR, CD20) |
| Proviral DNA (nested PCR/PBMC and LN) | Immunoblot and ELISA (seroconversion) |
| Quantitative virus isolation (PBMC) | Clinical signs and symptoms Ag specific IFN-γ, IL-2, IL-4, ELISPot ICS for IL-2 loss in CD4 subsets |

The relative merit of a vaccine regimen for future study are decided based on the outcome of the challenges and the observed potency, breadth, and durability of the immune responses pre- and post-challenge. In addition to the magnitude of the antigen-specific IL-2 responses (ELISPot) before challenge, the loss of Ag-specific IL-2 producing CD4 T-cell subsets as measured by ICS is prognostic of failure to contain/control virus load after challenge (see, also, Ogg et al. (199) *Science* 279(5359):2103-2106; Oldstone et al. (1997) *Virol.* 234(2): 179-185).

What is claimed is:

1. An immunogenic composition comprising an Env polypeptide of HIV and a small molecule CD4 mimetic, wherein the small molecule CD4 mimetic is {1-[(4,6-dimethyl-1H-indol-2-yl)carbonyl]piperidin-4-yl}(4-fluorophenyl)methanone.

2. An immunogenic composition comprising an Env polypeptide of HIV and a small molecule CD4 mimetic, wherein the small molecule CD4 mimetic is ethyl 1-[(4,6-dimethyl-1H-indol-2-yl)carbonyl]piperidine-4-carboxylate.

3. The immunogenic composition of claim 1 claim 2, wherein the Env polypeptide is a gp120 polypeptide.

4. The immunogenic composition of claim 1 or claim 2, wherein the small molecule CD4 mimetic is covalently attached to a cross-linking moiety.

5. The immunogenic composition of claim 1 or claim 2, wherein the small molecule CD4 mimetic is covalently attached to the Env polypeptide via a cross-linking moiety.

6. The immunogenic composition of claim 1 or claim 2, further comprising an adjuvant.

7. The immunogenic composition of claim 1 or claim 2 wherein the Env polypeptide and CD4 mimetic are in a complex.

8. The immunogenic composition of claim 1 or claim 2, wherein the Env polypeptide is a gp140 polypeptide.

9. The immunogenic composition of claim 1 or claim 2, wherein the Env polypeptide is a gp160 polypeptide.

10. The immunogenic composition of claim 4 wherein the small molecule CD4 mimetic is covalently attached to the cross-linking moiety via an intervening spacer.

* * * * *